United States Patent [19]
Purvis et al.

[11] Patent Number: 5,981,818
[45] Date of Patent: Nov. 9, 1999

[54] INTEGRATED CRACKING AND OLEFINS DERIVATIVE PROCESS UTILIZING DILUTE OLEFINS

[75] Inventors: David Purvis, Georgetown, Canada; Richard H. Mc Cue, Houston, Tex.

[73] Assignee: Stone & Webster Engineering Corp., Boston, Mass.

[21] Appl. No.: 08/734,036

[22] Filed: Oct. 18, 1996

Related U.S. Application Data

[63] Continuation-in-part of application No. 08/407,920, Mar. 21, 1995, abandoned.

[51] Int. Cl.$^6$ .................. C07C 4/02; C08F 2/34
[52] U.S. Cl. .......... 585/519; 585/251; 585/253; 585/271; 585/315; 585/330; 585/518; 585/648; 585/653; 568/469.9; 568/697; 568/850; 560/208; 560/210; 570/193; 526/75; 526/76; 526/901
[58] Field of Search .......... 526/75, 76; 585/518, 585/519, 650, 651, 652, 648, 326, 251, 253, 271, 315, 330, 653; 568/469.9, 697, 850; 560/208, 210; 570/193

[56] References Cited

U.S. PATENT DOCUMENTS

| | | | |
|---|---|---|---|
| 2,246,980 | 6/1941 | Lyons | 585/519 X |
| 2,775,577 | 12/1956 | Schneider et al. | 260/82 |
| 2,827,444 | 3/1958 | Cines | 260/88.1 |
| 2,964,504 | 12/1960 | Leary et al. | 260/82 |
| 3,280,095 | 10/1966 | Lyon | 260/94.9 |
| 3,392,211 | 7/1968 | Buschmann et al. | 260/683 |
| 3,403,722 | 10/1968 | Woebcke | 165/1 |
| 3,476,729 | 11/1969 | Smith et al. | 260/93.7 |
| 3,505,394 | 4/1970 | Olivier | 260/497 |
| 3,574,122 | 4/1971 | Payne et al. | 252/137 |
| 3,635,803 | 1/1972 | Binns et al. | 204/80 |
| 3,728,411 | 4/1973 | Siskin et al. | 260/668 |
| 3,839,475 | 10/1974 | Kurtz et al. | 260/660 |
| 3,850,993 | 11/1974 | Kylander et al. | 260/614 |
| 3,855,321 | 12/1974 | Bach et al. | 260/654 |
| 3,862,236 | 1/1975 | Scharff et al. | 260/603 |
| 3,892,816 | 7/1975 | Kister | 260/659 |
| 3,894,076 | 7/1975 | Van Duyne et al. | 260/486 |
| 3,907,882 | 9/1975 | Gaenzler et al. | 260/533 |
| 3,910,347 | 10/1975 | Woebcke | 165/142 |
| 3,925,452 | 12/1975 | Swodenk et al. | 260/497 |
| 3,929,898 | 12/1975 | Nienburg et al. | 260/604 |
| 3,985,820 | 10/1976 | Albright et al. | 260/683 |
| 4,008,290 | 2/1977 | Ward | 260/672 |
| 4,010,198 | 3/1977 | Roscher et al. | 260/497 |
| 4,061,659 | 12/1977 | Nielsen et al. | 260/348.34 |
| 4,143,075 | 3/1979 | Bryant | 260/604 |
| 4,172,099 | 10/1979 | Severino | 260/660 |
| 4,188,490 | 2/1980 | Hinnenkamp et al. | 560/245 |
| 4,230,668 | 10/1980 | Sheely et al. | 422/140 |
| 4,244,892 | 1/1981 | Guseinov et al. | 570/223 |
| 4,263,212 | 4/1981 | Hong et al. | 260/347 |
| 4,287,091 | 9/1981 | Selman | 252/429 |
| 4,288,649 | 9/1981 | McCaulay | 585/533 |
| 4,343,957 | 8/1982 | Sartorio et al. | 585/449 |
| 4,343,959 | 8/1982 | Kida et al. | 585/640 |
| 4,351,275 | 9/1982 | Bhojwani et al. | 122/7 |
| 4,403,080 | 9/1983 | Hughes | 526/76 |
| 4,426,449 | 1/1984 | Geigert et al. | 435/155 |
| 4,443,643 | 4/1984 | Watson et al. | 585/437 |
| 4,463,207 | 7/1984 | Johnson | 585/462 |
| 4,480,138 | 10/1984 | Hackman et al. | 568/454 |
| 4,508,842 | 4/1985 | Beran et al. | 502/112 |
| 4,521,631 | 6/1985 | Nishimura et al. | 568/478 |
| 4,524,229 | 6/1985 | Johnson | 585/463 |
| 4,554,392 | 11/1985 | Leuck et al. | 570/254 |
| 4,558,167 | 12/1985 | Riegel et al. | 570/238 |
| 4,558,170 | 12/1985 | Chen et al. | 585/532 |
| 4,590,317 | 5/1986 | Lenczyk | 570/220 |
| 4,634,794 | 1/1987 | Drake et al. | 560/245 |
| 4,647,690 | 3/1987 | Drake | 560/245 |
| 4,665,243 | 5/1987 | Burks, Jr. | 570/226 |
| 4,804,714 | 2/1989 | Olivo | 525/240 |
| 4,956,426 | 9/1990 | Ardell et al. | 526/60 |
| 4,966,951 | 10/1990 | Benham et al. | 526/106 |
| 4,992,608 | 2/1991 | Cavani et al. | 585/467 |
| 5,008,413 | 4/1991 | Liu | 549/534 |
| 5,011,980 | 4/1991 | Sano et al. | 560/245 |
| 5,035,732 | 7/1991 | McCue, Jr. | 62/24 |
| 5,055,627 | 10/1991 | Smith, Jr. et al. | 585/467 |
| 5,068,490 | 11/1991 | Eaton | 585/525 |
| 5,077,434 | 12/1991 | Sarumaru et al. | 562/534 |
| 5,079,266 | 1/1992 | Bockowski et al. | 514/703 |
| 5,102,841 | 4/1992 | Cann et al. | 502/112 |
| 5,144,090 | 9/1992 | Honda et al. | 568/476 |
| 5,183,936 | 2/1993 | Etzkorn et al. | 562/532 |
| 5,187,246 | 2/1993 | Baker et al. | 526/88 |
| 5,198,578 | 3/1993 | Etzkorn et al. | 562/532 |
| 5,210,354 | 5/1993 | Dubner et al. | 585/469 |
| 5,218,146 | 6/1993 | Takata et al. | 562/535 |
| 5,235,088 | 8/1993 | Paparizos et al. | 558/324 |
| 5,238,892 | 8/1993 | Chang | 502/111 |
| 5,243,111 | 9/1993 | Petit et al. | 570/243 |
| 5,243,115 | 9/1993 | Smith, Jr. et al. | 585/446 |
| 5,243,116 | 9/1993 | Lee et al. | 585/467 |
| 5,258,543 | 11/1993 | Suresh et al. | 558/325 |

(List continued on next page.)

FOREIGN PATENT DOCUMENTS

| | | |
|---|---|---|
| 0012147 | 6/1980 | European Pat. Off. . |
| 0612753 | 8/1994 | European Pat. Off. . |
| 72-042817 | 12/1968 | Japan . |
| 51-146410 | 12/1996 | Japan . |
| 528296 | 10/1976 | U.S.S.R. . |
| 1091174 | 11/1965 | United Kingdom . |
| 1071399 | 6/1967 | United Kingdom . |
| 1095727 | 12/1967 | United Kingdom . |
| 1264392 | 12/1974 | United Kingdom . |
| 1378330 | 12/1974 | United Kingdom . |
| 2039905 | 8/1980 | United Kingdom . |
| 9212184 | 7/1992 | WIPO . |

*Primary Examiner*—Fred Teskin
*Attorney, Agent, or Firm*—Hedman, Gibson & Costigan, P.C.

[57] ABSTRACT

A novel process is provided which integrates the cracking of hydrocarbon containing feedstocks with the olefins purification and olefins derivative process utilizing dilute olefin feedstocks.

24 Claims, 9 Drawing Sheets

U.S. PATENT DOCUMENTS

| | | | |
|---|---|---|---|
| 5,262,575 | 11/1993 | Dianis | 570/235 |
| 5,262,576 | 11/1993 | Smith, Jr. | 585/447 |
| 5,274,056 | 12/1993 | McDaniel et al. | 526/106 |
| 5,274,138 | 12/1993 | Keating et al. | 549/529 |
| 5,276,235 | 1/1994 | Dubner | 585/469 |
| 5,280,074 | 1/1994 | Schreck et al. | 525/240 |
| 5,288,473 | 2/1994 | Shaw et al. | 423/237 |
| 5,300,707 | 4/1994 | Caillod et al. | 568/480 |
| 5,314,614 | 5/1994 | Moser et al. | 208/262.1 |
| 5,342,907 | 8/1994 | Cann et al. | 526/129 |
| 5,349,072 | 9/1994 | Preston et al. | 549/529 |
| 5,364,915 | 11/1994 | Benham et al. | 526/105 |
| 5,378,779 | 1/1995 | Fauth et al. | 526/209 |
| 5,384,426 | 1/1995 | Ohyama et al. | 560/247 |
| 5,416,176 | 5/1995 | Hunt | 526/77 |
| 5,446,224 | 8/1995 | Miracca et al. | 585/324 |

5,981,818

INTEGRATED CRACKING AND OLEFINS DERIVATIVE PROCESS UTILIZING DILUTE OLEFINS

The present application is a continuation-in-part application of U.S. Ser. No. 08/407,920, filed Mar. 21, 1995, attorney docket 696-243, now abandoned.

FIELD OF THE INVENTION

The present invention relates to a method of integrating cracking and olefin derivative processes utilizing dilute olefins as feedstocks. More particularly the present invention relates to an integrated process for preparing olefin derivatives from hydrocarbon feedstocks by cracking the hydrocarbon feedstocks, and separating the olefins from the cracked gas into dilute olefin feeds for olefin derivative processing. Most particularly, the present invention relates to an integrated process for manufacturing ethylene and propylene derivatives from catalytic and non-catalytic cracking processes.

BACKGROUND OF THE PRESENT INVENTION

The processes of non-catalytically cracking and catalytically cracking hydrocarbon feedstocks are well known in the art. In this regard, steam cracking in a furnace and contact with hot non-catalytic particulate solids are two well known non-catalytic cracking processes, as described, for example in Hallee et al., U.S. Pat. No. 3,407,789; Woebcke, U.S. Pat. No. 3,820,955, DiNicolantonio, U.S. Pat. No. 4,499,055 and Gartside et al., U.S. Pat. No. 4,814,067. Additionally, fluid catalytic cracking and deep catalytic cracking are two well known catalytic cracking processes. See, e.g., Cormier, Jr. et al., U.S. Pat. No. 4,828,679; Rabo et al., U.S. Pat. No. 3,647,682; Rosinski et al., U.S. Pat. No. 3,758,403; Gartside et al., U.S. Pat. No. 4,814,067; Li et al., U.S. Pat. No. 4,980,053; and Yongqing et al., U.S. Pat. No. 5,326,465.

The olefins produced in these processes have long been desired as feedstocks for the petrochemical industries. Olefins such as ethylene, propylene, the butenes and the pentenes are useful in preparing a wide variety of end products, including but not limited to polyethylenes, polypropylenes, polyisobutylene and other polymers, alcohols, vinyl chloride monomer, acrylo-nitrile, methyl tertiary butyl ether and tertiary amyl methyl ether and other petrochemicals, and a variety of rubbers such as butyl rubber.

However, there has been little incentive in the industry to integrate the cracking processes which produce the olefins with the olefin derivative processes which produce the end products due to either the inability of the respective processes to handle dilute olefin feeds, the difficulty in recycling the by-products produced in the respective processes or both as well as logistical reasons.

For example, in the polymerization processes to produce polyethylene and polypropylene, historically the location and infrastructure associated with ethylene-polyolefin units has made integration a difficult logistics problem. More importantly, recycle streams from the polyolefins units have until recently contained corrosive products from the catalyst deactivation reactions and other impurities.

Additionally, the feedstocks conventionally required for the production of polyethylenes and polypropylenes have demanded that methane, ethane and propane concentrations in the ethylene and propylene feedstocks be extremely low. For example, for ethylene, the minimum concentration of ethylene is typically about 99.9 mol % and for propylene the minimum propylene concentration for polymer grade propylene is typically about 99.0 mol %.

These ethylene and propylene feedstock specifications have required extensive and costly purification in the olefin recovery section of the cracking processes. Typically, the ethylene concentration in the $C_2$ stream from a cracker gas separation system ranges from about 55 to about 85 percent. The higher purity ethylene stream conventionally requires additional separation in a $C_2$ splitter.

Still further, advancements in polymerization catalysis, with the introduction of the "single site" metallocene catalysts, have resulted in even more stringent feedstock purity requirements due to the expanding usage of these high activity catalysts. See, e.g., Chang, U.S. Pat. No. 5,238,892; Burkhardt et al., PCT Application No. WO 9212184; and Schreck et al., U.S. Pat. No. 5,280,074.

Accordingly, the conventional wisdom in the industry is for olefin derivative producers, including, polyethylene and polypropylene producers, to purchase polymer grade ethylene and propylene from ethylene and propylene producers and then remove trace contaminants to the desired purity specifications and recover, flare or utilize the purge streams from the olefin derivative reactor within the processing plant.

Traditionally, ethylene and propylene unit operators have not accepted the recycle streams from the olefin derivative units because they typically contain undesirable light gases and inorganic acids resulting from catalyst deactivation reactions.

However, with ethylene and propylene units now being built in more remote and unsophisticated locations close to feedstock supply sources, it has now become desirable to develop a single integrated process which will produce the desired olefin derivative products as the final output of the integrated plant.

Additionally, existing refineries have long experienced problems of gas plant bottlenecking when increasing the capacity or conversion level of their various cracking units. The inability to market the relatively dilute olefins produced in the refinery to downstream purification processors has further compounded the problem. Thus, it has also become desirable to develop a means of revamping an existing refinery to debottleneck the gas plant and market the dilute olefins produced therein.

Accordingly, if such a means to integrate cracking with olefins derivative processes were to be developed it would represent a significant advancement in the state of the art including the realization of significant capital and operating cost savings for end product producers.

SUMMARY OF THE PRESENT INVENTION

To this end, the present inventors have now discovered a unique integrated process to overcome the drawbacks of the prior art and meet the commercially desirable aspects discussed above.

Accordingly, it is an object of the present invention to provide a process which will integrate olefins production with olefins derivative facilities in a "grassroots" design or revamp/expansion of an existing olefins facility.

It is another object of the present invention to provide a process which will integrate the cracking of hydrocarbons with ethylene polymerization and/or other ethylene derivative units.

It is a further object of the present invention to provide an integrated process which allows for the production of polyethylene and/or other suitable ethylene derivatives from a relatively dilute ethylene feedstock.

It is a still further object of the present invention to provide a process which will integrate the cracking of hydrocarbons with propylene polymerization and/or other propylene derivative units.

It is still another object of the present invention to provide an integrated process which allows for the production of polypropylene and/or other suitable propylene derivatives from a relatively dilute propylene feedstock.

It is yet another object of the present invention to provide a process which integrates a cracking process with one or more olefin derivative processes.

It is another further object of the present invention to provide an integrated process which provides for the recycling of the olefin derivative by-product streams to the cracking unit.

It is still another further object of the present invention to integrate processes for the production of polymers, rubbers and petrochemicals from the $C_4$ hydrocarbons derived from the cracking process with the olefin derivative processes and cracking process.

It is yet still another further object of the present invention to integrate dilute olefin derivative processes with existing refinery offgas systems to debottleneck the refineries.

These and other objects evident to those of ordinary skill in the art are provided by the present invention discussed in detail hereinbelow.

DETAILED DESCRIPTION OF THE PRESENT INVENTION

Figure 1:
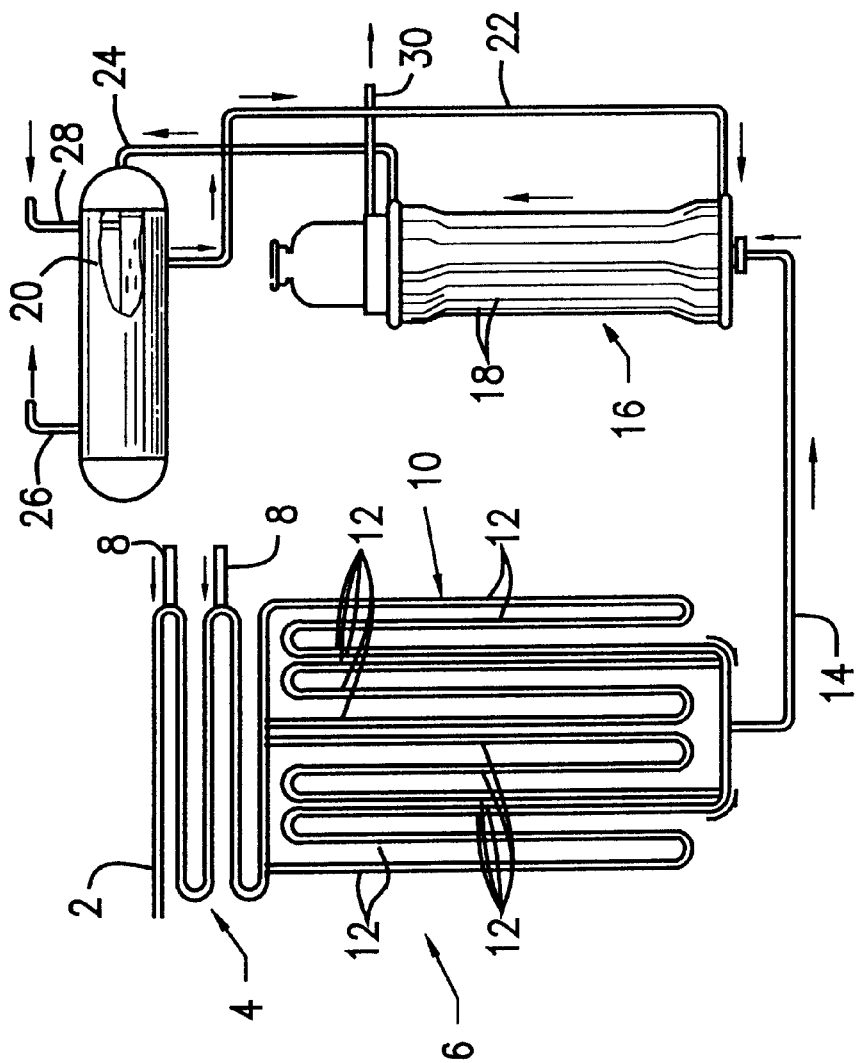
FIG. 1 depicts in flow chart form a steam cracking process useful in the practice of the present invention.

As used herein throughout the present specification the term "dilute olefins" means olefins which meet the non-saturated hydrocarbon and other trace contaminant specifications of the respective olefins derivative process but still contain quantities of saturated inert hydrocarbons in excess of typical current polymer grade specifications, such as on the order of less than about 50 weight percent, preferably less than about 15 weight percent and most preferably as little as 1 weight percent.

Also as used herein throughout the present specification, the term "olefin derivative process" is meant to include any and all processes whereby olefins are converted to petrochemical products or intermediates in a relatively high conversion once through process, i.e., the bulk of the olefins are converted to the desired petrochemical in a single process sequence without the need for recycle or further processing steps, at high once through conversions typically on the order of at least about 50 percent, preferably at least about 75 percent and, in the ideal case, up to about 100 percent.

THE FEEDSTOCKS

The hydrocarbon feedstocks for use in the cracking processes of the present invention may vary widely and are well known to those of ordinary skill in the art. All of the known hydrocarbon feedstocks for use in the cracking processes described hereinbelow are contemplated for use in accordance with the present invention. For example, feedstocks for use in accordance with the present invention include, but are not limited to, ethane, propane, butane, naphtha, raffinate, atmospheric gas oil, vacuum gas oil, gas condensates, natural gas liquids, crude oil, crude resids, mixtures thereof, etc.

THE CRACKING PROCESSES

The process of the present invention may employ any cracking process which produces a cracked gas, such as those containing hydrogen, methane, $C_2$ hydrocarbons, $C_3$ hydrocarbons and heavier constituents. This includes both catalytic and non-catalytic cracking processes.

The steam cracking process and other non-catalytic cracking processes are well known to those of ordinary skill in the art. Steam cracking processes are generally carried out in radiant furnace reactors at elevated temperatures for short residence times while maintaining a low reactant partial pressure, relatively high mass velocity, and effecting a low pressure drop through the reaction zone. Any of the furnaces known to those skilled in the art may be employed in the practice of the present invention, e.g., Bowen et al., U.S. Pat. No. 5,151,158; Palchik et al., U.S. Pat. No. 3,274,978; Hallee et al., U.S. Pat. No. 3,407,789; Woebcke, U.S. Pat. No. 3,820,955; Alagy et al., U.S. Pat. No. 4,780,196; DiNicolantonio, U.S. Pat. No. 4,499,055; Martens, U.S. Pat. No. 4,762,958 and the like.

The hydrocarbon feed to the steam cracker can be in the liquid or vapor phase or it may comprise a mixed liquid-vapor phase. The most preferred feedstocks for steam cracking are ethane, propane, butane, naphtha, gas oils, gas condensates and mixtures thereof. The hydrocarbon feedstock is normally in the vapor phase in the reaction zone.

Referring to FIG. 1, the feed will generally be preheated in a preheat zone (not shown) from about ambient temperature, e.g., 70° F. to 80° F., to an intermediate temperature. The preheated feed in a line 2 is then introduced into a convection zone 4 of a pyrolysis furnace 6 to further preheat the feed to a temperature below which no significant reaction takes place, e.g., 1100° F. to 1300° F. During the convection zone preheating step, steam is generally added to the feed via lines 8 to essentially complete vaporization of the feed prior to the feed being introduced to the radiant reaction zone 10 of the pyrolysis furnace 6. The steam functions to facilitate vaporization and reduce the hydrocarbon partial pressure in the radiant reaction zone in order to improve desired olefin yields. The feed in process tubes or coils 12 is then cracked at very high temperatures, e.g., up to about 1650° F., in the radiant reaction zone 10 of the pyrolysis furnace 6.

Typical operating conditions comprise an inlet temperature to the radiant heating section of the furnace ranging from about 1000° F. to about 1300° F. and an outlet temperature ranging from about 1350° F. to about 1650° F. The feed rate is such that the velocity through the radiant coils 12 ranges from about 200 ft/sec to about 800 ft/sec, based on the total flow of steam and hydrocarbon. Steam is typically employed in amounts to provide a steam to hydrocarbon feed weight ratio ranging from about 0.1 to about 2.0. The residence time of the feed in the radiant section of the cracking coil generally ranges from about 0.1 second to about 1 second, although millisecond processes are also contemplated as within the scope of the present invention.

In order to reduce the production of large amounts of undesirable by-products and in order to prevent severe coking, it is desirable to rapidly cool the effluent product gases issuing from the radiant zone from its exit temperature to a temperature at which the cracking reactions substantially stop. This can be accomplished in a suitable heat exchange apparatus or by direct quenching, wherein the product gases are cooled to a temperature below about 1200° F. to stop the cracking reaction. Further cooling is typically achieved in high level heat recovery as is known to those of ordinary skill in the art. The cooling step is preferably carried out very rapidly after the effluent leaves the radiant section of the furnace, i.e., about 1 to 30 milliseconds. See generally, e.g., Hallee et al., U.S. Pat. No. 3,407,789, Woebcke, U.S. Pat. No. 3,910,347, Woebcke et al., U.S. Pat. No. 5,427,655, Buschmann et al., U.S. Pat. No. 3,392,211, Bhojwani et al., U.S. Pat. No. 4,351,275, Woebcke, U.S. Pat. No. 3,403,722, Buschmann et al., United Kingdom Patent No. 1,095,727 and Buschmann et al., United Kingdom Patent No. 1,091,174.

As shown in FIG. 1, the cracked effluent from the pyrolysis reactor in a line 14 is directed to a quench boiler 16 wherein the effluent is indirectly contacted with boiler feed water in cooling tubes 18. The boiler feed water is supplied via a tank 20 which directs water to the bottom of the quench boiler 16 via a line 22. After traverse of the cooling tubes 18, a steam/water mixture is removed from the quench boiler 16 in a line 24 and directed back to the supply tank 20. The supply tank 20 has high pressure steam removed therefrom in a line 26 and make up boiler feed water added thereto in a line 28. The quenched product gases are removed from the quench boiler 16 via a line 30 for recovery of the dilute olefins and downstream processing into various petrochemicals.

Alternatively, instead of steam cracking other well known cracking processes may be employed to produce olefins including thermal regenerative cracking, fluidized bed cracking, fluid catalytic cracking, deep catalytic cracking, visbreaking, etc.

In thermal regenerative cracking (TRC), inert particulate solids are heated to relatively high temperatures, on the order of from about 1400° F. to about 1600° F., and introduced into a fluidized cracking zone with the hydrocarbon feed. The cracking zone may be upflow (riser), downflow or horizontal in configuration. The hydrocarbon feed is thermally cracked at temperatures ranging from about 1200° F. to about 1600° F. in the cracking zone wherein the heated particulate solids lose heat and are fouled or contaminated with the coke and tars and other heavy cracking products of the hydrocarbon feed. Thereafter, the contaminated solids are separated from the hydrocarbon product gases, stripped and regenerated for re-use in the cracking zone. Regeneration entails burning the contaminants from the particulate solids to heat the solids to a temperature necessary to crack the hydrocarbon feed. See, e.g., Gartside et al., U.S. Pat. No. 4,814,067, Boston, U.S. Pat. No. 2,906,695; Woebcke et al., U.S. Pat. No. 4,318,800; McKinney et al., U.S. Pat. No. 4,061,562; McKinney et al., U.S. Pat. No. 4,097,363 and Gartside et al., U.S. Pat. No. 4,552,645.

In fluidized catalytic cracking (FCC), the process proceeds similar to that described for thermal regenerative cracking except that the solids are catalytic and the temperatures employed are generally lower, with cracking temperatures on the order of from about 800° F. to about 1300° F. Any of the known catalysts useful in fluidized catalytic cracking may be employed in the practice of the present invention, including but not limited to Y-type zeolites, USY, REY, RE-USY, faujasite and other synthetic and naturally occurring zeolites and mixtures thereof. See, e.g., Gartside et al., U.S. Pat. No. 4,814,067; Haddad et al., U.S. Pat. No. 4,404,095; Cartmell, U.S. Pat. No. 3,785,782; Castagnos, Jr. et al., U.S. Pat. No. 4,419,221; Cormier, Jr. et al., U.S. Pat. No. 4,828,679; Rabo et al., U.S. Pat. No. 3,647,682; Rosinski et al., U.S. Pat. No. 3,758,403; and Dean et al., U.S. Reissue Pat. No. RE 33,728.

Another cracking process contemplated for use in accordance with the present invention is deep catalytic cracking (DCC). In the DCC process a preheated hydrocarbon feedstock is cracked over heated solid acidic catalyst in a reactor at temperatures ranging from about 925° F. to about 1350° F., preferably from about 1025° F. to about 1150° F. The weight hourly space velocity of the charge may range from about 0.2 $hr^{-1}$ to about 20 $hr^{-1}$ preferably from about 1 $hr^{-1}$ to about 10 $hr^{-1}$. The catalyst-to-oil ratio may vary from about 2 to about 12, preferably from about 5 to about 10. In order to lower the partial pressure of hydrocarbon feed, steam or other gases, such as the dry gas of a catalytic cracking unit, may be added into the reactor during the conversion process.

When steam is used, a weight ratio of steam to hydrocarbon feed is preferably maintained at from about 0.01 to about 0.5:1. The total pressure of the reaction preferably ranges from about 20 psia to about 45 psia, more preferably from about 25 psia to about 35 psia.

After the reaction, the spent catalyst particles may be steam stripped to remove residual hydrocarbons absorbed on the catalyst as is known in the art. The spent catalyst particles with coke deposited thereon are then transferred to a regeneration zone as is also well known to those of ordinary skill in the art.

Regeneration is generally conducted by contacting the catalyst with an oxygen-containing gas at a temperature of from about 1175° F. to about 1350° F. Afterwards the regenerated catalyst is typically recycled to the reaction zone.

Hydrocarbon feedstocks useful in the DCC process may vary in a wide range, and typically are relatively heavy hydrocarbon feedstocks such as those selected from petroleum fractions with different boiling ranges, i.e., naphtha, gas oil, vacuum gas oil, residual oil and mixtures thereof. Crude oil may also be directly used.

Catalysts used in the deep catalytic cracking process step of the present invention are solid, acidic catalysts comprising one or more active components and a matrix material. The active components include amorphous aluminosilicates or zeolites such as pentasil shape selective molecular sieves, faujasite, rare earth cation exchanged faujasite, chemically treated and/or stabilized faujasite and mixtures thereof. The matrix material includes synthetic inorganic oxides and mineral clays. All of these catalysts are commercially available.

Exemplary of the useful catalysts are pentasil shape molecular sieves, rare earth exchanged Y sieve (REY) containing catalysts, pentasil shape molecular sieves supported on kaolinite, amorphous aluminosilicates and mixtures of any of the foregoing.

The use of these catalysts at the specified reaction conditions provides for high yields of gaseous olefins, especially propylene and butylenes. For a more detailed description of the DCC process, its catalyst and variations on the DCC process, see, Li et al., U.S. Pat. No. 4,980,053; Shu et al., U.S. Pat. No. 5,232,675; Zhicheng et al., U.S. Pat. No. 5,380,690; Yongqing et al., U.S. Pat. No. 5,326,465 and Yukang et al., U.S. Pat. No. 5,358,918.

It is further contemplated by the present invention that one or more of the above described cracking processes may be employed, either as separate cracking processes to crack different feedstocks, or in an integrated method such as described in Rubin et al., U.S. Pat. No. 5,523,502.

THE RECOVERY PROCESSES

The gaseous effluent from the cracking reaction is then directed to an olefins purification system for recovery of the dilute olefins. Typically the gaseous effluent is further cooled to remove fuel oil and the bulk of dilution steam, as known to those of ordinary skill in the art, prior to being compressed in a charge gas compressor and then chilled and passed through a series of pressurized fractionators to separate the effluent into component streams, e.g., hydrogen, methane, ethane, propane, ethylene, propylene, mixed $C_4$ hydrocarbon streams, and $C_{5+}$ material. Conventional fractionation units are described in Roberts, U.S. Pat. No. 2,582,068; Rowles et al., U.S. Pat. Nos. 4,002,042, 4,270,940, 4,519,826 and 4,732,598; and Gazzi, U.S. Pat. No. 4,657,571. See also, Kaiser et al., "Hydrocarbon Processing," Nov. 1988, pp. 57–61.

Especially suitable olefins purification processes for use herein are the cryogenic separation processes described in McCue et al., U.S. Pat. Nos. 4,900,347 and 5,035,732 which employ serially connected dephlegmators upstream of serially connected demethanizers to cryogenically separate the gaseous mixtures into their component parts. Additionally, the process set forth in McCue et al., U.S. Pat. No. 5,414,170 providing for a mixed phase front end acetylene hydrogenation process is also contemplated for use in the present invention.

Thus, in a preferred embodiment, the product gases are compressed in a charge gas compressor, dried, then the acetylene components are hydrogenated in an acetylene hydrogenation reactor, and finally passed into the cryogenic chilling train.

In the preferred cryogenic chilling train the gas charge is passed through serially connected dephlegmators to separate the hydrogen and most of the methane gas from the charge. The remaining charge is then further separated into its component parts by use of serially connected towers comprising one or more of demethanizer(s), deethanizer(s), deethylenizer(s), depropanizer(s), $C_2$ and $C_3$ splitters, etc., to produce streams rich in the component parts.

In an especially preferred embodiment the olefins purification process comprises a compression system and a cryogenic separation process for recovering a plurality of component effluent streams comprising one or more of an ethane-rich stream, a propane-rich stream, a dilute ethylene stream, a dilute propylene stream, a mixed $C_4$ hydrocarbon-rich stream, and a gasoline-rich stream from the mixed olefin-containing effluent, wherein the cryogenic separation process comprises (A) introducing the mixed olefin containing-effluent into a dephlegmation or separation zone operating at cryogenic temperatures; (B) dephlegmating or separating the mixed olefin-containing effluent into a primary hydrogen and methane-rich gas stream and a primary liquid condensate stream rich in $C_{2+}$ hydrocarbon components and containing a minor amount of methane; (C) separating the primary liquid condensate stream in a moderately low cryogenic temperature primary demethanizer unit into a $C_{2+}$ liquid bottoms stream and an intermediate methane-rich substantially $C_3$ free overhead vapor stream; (D) separating the intermediate methane-rich overhead vapor stream in an ultra low cryogenic temperature final demethanizer into a dilute ethylene product stream and a final demethanizer ultra-low temperature methane stream; and (E) separating the $C_2^+$ liquid bottoms stream from the primary demethanizer in at least one downstream fractionator into effluent streams comprising one or more of an ethane-rich stream, a propane-rich stream, a second dilute ethylene stream, a dilute propylene stream, a $C_4$ hydrocarbon-rich stream and a gasoline-rich stream.

The dilute ethylene and dilute propylene product streams may then be used as the dilute ethylene and dilute propylene feedstocks for the downstream integrated olefin derivative processes, as described more fully hereinbelow. The ethane-rich and propane-rich streams are typically recycled to the cracking reactor.

Figure 2:
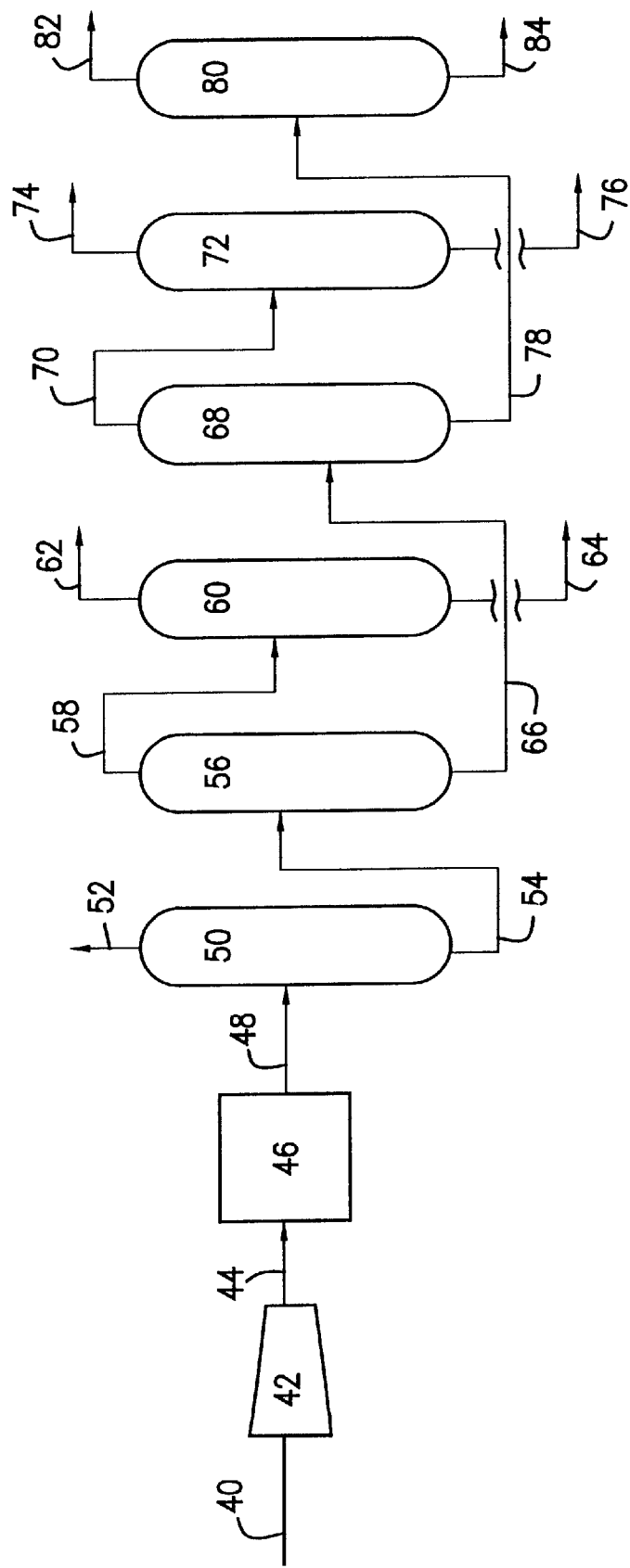
FIG. 2 depicts in flow chart form an olefins purification process useful in the practice of the present invention.

Alternatively, an olefins purification system as shown in FIG. 2 may be employed. The cracked gas effluent in a line 40 is first compressed in a compressor 42 to produce a compressed gas effluent in a line 44. Acid gas is removed from the stream, the acetylene is then removed via conversion and the stream dried and chilled in system 46 to produce a chilled effluent in a line 48.

The chilled effluent is directed to a demethanizer 50 wherein methane and lighter gases are separated from the heavier components. The methane is removed from the overhead in a line 52. The heavier components are removed from the bottom of the demethanizer 50 in a line 54 and directed to a deethanizer 56 for separation of the ethane and ethylene from the heavier components. Accordingly, a dilute ethylene stream comprising ethane and ethylene is removed from the top of the deethanizer 56 in a line 58. All or a portion of the dilute ethylene stream may then optionally be directed to a $C_2$ splitter 60, wherein the ethane and ethylene are separated into a second dilute ethylene stream in a line 62 and an ethane-rich stream in a line 64 if higher purity dilute ethylene is desired.

The bottoms from the deethanizer 56 rich in $C_3$ and heavier components are removed from the deethanizer 56 in a line 66 and directed to a depropanizer 68 for separation of propane and propylene from the heavier components. Accordingly, a dilute propylene stream is removed from the top of the depropanizer 68 in a line 70. All or a portion of the dilute propylene stream may then optionally be directed to a $C_3$ splitter 72 wherein the propane and propylene are separated into a second dilute propylene stream in a line 74 and a propane-rich stream in a line 76 if higher purity dilute propylene is desired.

The bottoms from the depropanizer 68 rich in $C_4$ and heavier components are removed from the depropanizer 68 in a line 78 and directed to a debutanizer 80 for separation of the $C_4$ hydrocarbons from the heavier components. Accordingly, a mixed $C_4$ hydrocarbon-rich stream is removed from the overhead of the debutanizer 80 in a line 82, and the gasoline and heavier components are removed from the bottom of the debutanizer 80 via a line 84.

The dilute ethylene, dilute propylene and mixed $C_4$ hydrocarbon-rich streams may then be processed into a variety of petrochemicals in accordance with the practice of the present invention. The ethane- and propane-rich streams in lines 64 and 76, respectively, are then generally recycled back to the cracking reactor.

THE OLEFIN DERIVATIVE PROCESSES

Polyethylene

The dilute ethylene stream obtained from the olefins purification process may be employed as the dilute ethylene feedstock for a polyethylene polymerization process in accordance with the present invention. The dilute ethylene feedstock for use in the polyethylene polymerization process preferably contains at least about 85 weight percent ethylene.

The ethylene is polymerized into polyethylene either by gas phase polymerization methods or by solution polymerization methods. At ethylene feedstock concentrations above about 85% but below about 95%, the solution polymerization method is employed. At concentrations of at least about 95 weight percent, either the gas phase or solution polymerization methods may be employed.

Both the gas phase and solution polymerization methods are well known to those of ordinary skill in the art and any of these known methods may be employed in the practice of the present invention. These processes are typically offered in the industry by companies including but not limited to Union Carbide Corporation, British Petroleum Company, Novacor, DSM et al. Typical operating parameters include pressures ranging from about 300 psig to about 3000 psig and temperatures ranging from about 200° F. to about 600° F. over catalysts such as those of the Ziegler-Natta (Z/N) family and the "single site" metallocene family. See, e.g., Benham et al., U.S. Pat. No. 5,364,915; Chang, U.S. Pat. No. 5,238,892; Cann et al., U.S. Pat. No. 5,102,841; Beran et al., U.S. Pat. No. 4,508,842; Geerts et al., European Patent No. 0 612 753; Wagner et al., European Patent No. 0 012 147; Karol, Frederick J., "The Polyethylene revolution," Chemtech, April 1983, pp. 222–28; and "New route to low-density polyethylene," Chemical Engineering, Dec. 3, 1979, pp. 80–85. See also, Hatch & Matar, "From Hydrocarbons to Petrochemicals," (hereinafter "HATCH & MATAR") pp. 172–176.

The practice of the present invention also provides significant unexpected advantages for the gas phase process over the current commercially practiced gas phase processes for the production of polyethylene. In the current commercially practiced gas phase processes, nitrogen is employed as the carrier gas to the gas phase polyethylene polymerization reactor. This expedient creates unwanted by-products for recycling to the cracking reactor in the olefins unit. However, with the practice of the present invention employing dilute ethylene feedstock for the gas phase polymerization, the methane or ethane (or other light saturated hydrocarbon) contained in the dilute ethylene feedstock is effective as the carrier gas thus eliminating or significantly reducing the aforementioned recycling problem.

Other Alternative Ethylene Derivative Units

Dilute ethylene can generally be employed in any derivative process which achieves high once through conversion of the ethylene. Processes, including but not limited to processes for the production of ethylene dichloride, alpha olefins, ethyl benzene, styrene and acetaldehyde are contemplated as within the scope of the present invention. The specifics of these processes are disclosed in the literature and are well known to those of ordinary skill in the art. See, for example, HATCH & MATAR, pp. 97–98; Kurtz et al., U.S. Pat. No. 3,839,475; Severino, U.S. Pat. No. 4,172,099; Geigert et al., U.S. Pat. No. 4,426,449; Leuck et al., U.S. Pat. No. 4,554,392; HATCH & MATAR, pp. 137–138; Smith, Jr. et al., U.S. Pat. No. 5,243,115; Lee et al., U.S. Pat. No. 5,243,116; HATCH & MATAR, pp. 138–140; Hong et al., U.S. Pat. No. 4,263,212; HATCH & MATAR, pp. 99–101; Nishimura et al., U.S. Pat. No. 4,521,631; and Showa Denko, JP 51-146410.

Polypropylene

The dilute propylene stream obtained from the olefins purification process step may be employed as the dilute propylene feedstock for a polypropylene polymerization process in accordance with the present invention. The dilute propylene feedstock for polypropylene polymerization preferably contains at least about 85 weight percent propylene and most preferably at least about 95 weight percent propylene.

The propylene is polymerized into polypropylene homopolymer either by bulk phase polymerization methods or by gas phase polymerization methods. At propylene feedstock concentrations below 95%, the bulk phase polymerization method is employed. At concentrations of at least about 95 weight percent, either the bulk phase or gas phase polymerization methods may be employed.

Both the bulk phase and gas phase polypropylene polymerization methods are well known to those of ordinary skill in the art and any of these known methods may be employed in the practice of the present invention or a combination of both. These processes are offered in the industry by companies including, but not limited to, Union Carbide Corporation, Amoco Oil Company and Himont now (Montell). Typical operating parameters include pressures ranging from about 150 psig to about 1000 psig and temperatures ranging from about 200° F. to about 600° F. over catalysts such as those of the Ziegler-Natta family (Z/N) and the "single site" metallocene family. See, e.g., Schreck et al., U.S. Pat. No. 5,280,074; Ardell et al., U.S. Pat. No. 4,956,426; and Selman et al., U.S. Pat. No. 4,287,091. See also, HATCH & MATAR, pp. 176–79.

Following the polypropylene homopolymer polymerization process, the polypropylene homopolymer is typically copolymerized with ethylene, i.e, 2 to 15 weight percent ethylene, in an impact reactor. In either propylene polymerization process, the impact reactor operates in the gas phase at operating parameters of a pressure ranging from about 150 psig to about 400 psig and a temperature ranging from about 200° F. to about 400° F. over catalysts such as those of the Ziegler-Natta (Z/N) family as well as the "single site" metallocene family.

Other Alternative Propylene Derivative Units Dilute propylene can also be employed in a number of other derivative processes which achieve high once through conversion of the propylene. Potential applications would include, but not be limited to, acrylonitrile, cumene, propylene oxide, isopropanol, acrolein, allyl chloride, etc. The specifics of these processes are disclosed in the literature and are well known to those of ordinary skill in the art. See, for example, HATCH & MATAR, pp. 106–108; Shaw et al., U.S. Pat. No. 5,288,473; Suresh et al., U.S. Pat. No. 5,258,543; Paparizos et al., U.S. Pat. No. 5,235,088; HATCH & MATAR, pp. 108–112; Binns et al., U.S. Pat. No. 3,635,803; Preston et al., U.S. Pat. No. 5,349,072; Keating et al., U.S. Pat. No. 5,274,138; HATCH & MATAR, pp. 112–115; HATCH & MATAR, pp. 115–117; Etzkorn et al., U.S. Pat. No. 5,198,578; Etzkorn et al., U.S. Pat. No. 5,183,936; Honda et al., U.S. Pat. No. 5,144,090; Caillod et al., U.S. Pat. No. 5,300,707; HATCH & MATAR, pp. 119; Dianis, U.S. Pat. No. 5,262,575; Riegel et al., U.S. Pat. No. 4,558,167; Guesinov et al., U.S. Pat. No. 4,244,892; Bach et al., U.S. Pat. No. 3,855,321; Riegel et al., United Kingdom Patent No. GB 2,039,905; HATCH & MATAR, p. 140; Smith, Jr., U.S. Pat. No. 5,262,576; Lee et al., U.S. Pat. No. 5,243,116; Johnson, U.S. Pat. No. 4,463,207; Cavani et al., U.S. Pat. No. 4,992,608; Ward, U.S. Pat. No. 4,008,290; Johnson, U.S. Pat. No. 4,524,229; Sartorio et al., U.S. Pat. No. 4,343,957; and Smith, Jr. et al., U.S. Pat. No. 5,055,627.

RECYCLING

Essential to the practice of the present invention is the expedient of recycling at least a portion of the by-product stream from the olefin derivative process to the cracking step. The recycling may be accomplished either directly or indirectly. In the embodiment of direct recycle, all or a portion of the by-product stream is directly recycled to the cracking reactor along with the fresh or recycled hydrocarbon feedstock. The direct recycle method is typically employed where there are sufficiently small amounts of contaminants such that the cracking process is not detrimentally affected.

In the embodiment of the indirect recycle, all or a portion of the by-product stream from the particular olefin derivative is first recycled to the olefins purification process step or to a separate clean up system (as known to those of ordinary skill in the art) within the integrated complex for removal of contaminants which are detrimental to the cracking process. Then, the derivative by-products as a portion of the recycle from the olefins purification process, such as in the ethane or propane-rich streams is recycled to the cracking reactor.

In either manner, direct or indirect recycle, at least a portion of the by-product stream from the olefin derivative process is recycled to the cracking reactor in order to form an integrated process and obtain the advantages over the prior art described hereinabove.

$C_4$ PROCESSING

Where naphtha or other liquid hydrocarbons are employed as the feedstock to the integrated process of the present invention, sufficient amounts of butylenes are produced in the cracking process and separated during the olefins purification step for conversion to $C_4$ containing petrochemical products and intermediates such as methyl tert butyl ether, isobutylene, butyl rubber and/or methyl methacrylate. In a preferred embodiment, especially useful in the practice of the present invention, the $C_4$ hydrocarbons are converted to the desired petrochemicals by a process including one or more of the steps of hydroisomerization, skeletal isomerization and, extractive distillation. These processes are discussed more fully hereinbelow.

DEBOTTLENECKING

The present invention also provides a novel means and apparatus for debottlenecking an existing cracking plant. Generally expansion of existing olefins facilities is limited by the amount of available refrigeration or fractionation capability or both. Making at least a portion of the olefins in a dilute form for use as a feedstock in an olefin derivative process would greatly increase the expansion potential of these facilities. Coupling the incremental olefins product (in dilute form) with a process that can accept dilute olefin feedstock as described in this invention would significantly improve the expansion potential and overall profitability of the complex.

Accordingly, the present invention provides such an expansion means. The present invention contemplates the integrating the existing facility with an olefins purification system to produce dilute olefins and one or more olefins derivative processes to process the incremental dilute olefins. Because the present invention provides for the integration of one or more olefins derivative processes with the olefins facility instead of marketing the dilute olefins to downstream purification processors, the present invention provides the simple debottlenecking means long sought in the art. The present invention thereby further enables the petrochemical producer to realize significant capital and operating cost savings. This concept is especially well suited for adaptation with an Advanced Recovery System (ARS) process or revamp as described in U.S. Pat. Nos. 4,900,347; 5,035,732 and 5,414,170.

DESCRIPTION OF THE PREFERRED EMBODIMENTS

The following description of preferred embodiments are intended for illustration purposes only and are not to be construed to limit the scope of the claims in any manner whatsoever.

Figure 3:
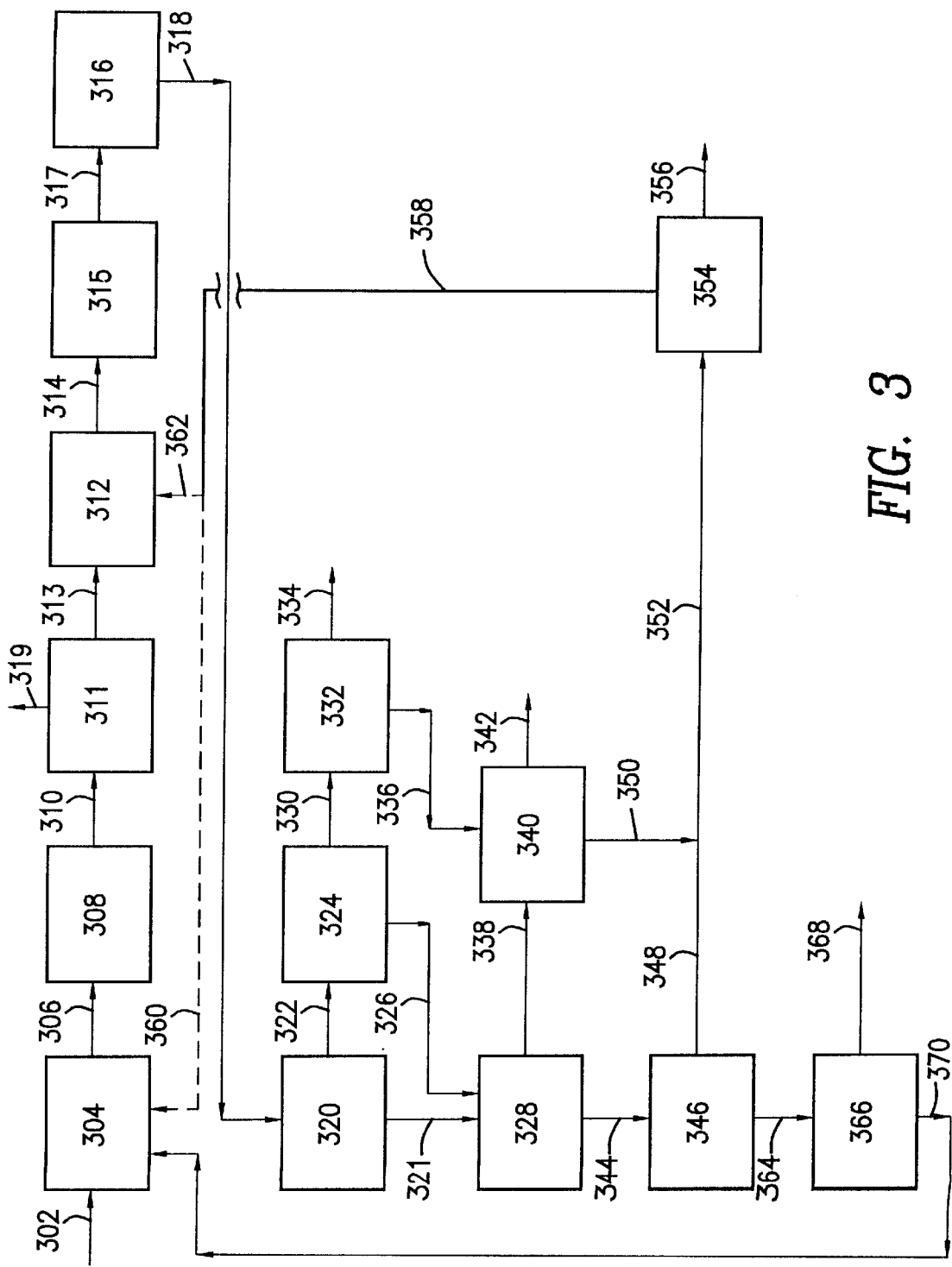
FIG. 3 depicts in flow chart form an embodiment of an integrated process for the production of polyethylene in accordance with the present invention.

Turning to FIG. 3, there is shown a process for the practice of the present invention to produce polyethylene from an ethane feedstock.

An ethane feedstock in a line 302 is directed to a steam cracker 304 for cracking to ethylene and other by-products. In order to prevent production of large amounts of the by-products and in order to prevent severe coking in the product line 306 from the steam cracker 304, it is desirable to cool rapidly the effluent product gases issuing from the radiant zone from an exit temperature of from about 1500° to about 1650° F. to a temperature at which the cracking reactions substantially stop. This can be accomplished by passing the cracked product to a quench boiler 308 for indirect quenching.

At ethane conversion levels between 55% and 75% in a steam cracker, a typical steam cracking yield of an ethane feedstock issuing from the quench boiler 308 in a line 310 comprises from about 1 to about 5 weight percent $H_2$, from about 3 to about 10 weight percent $CH_4$, less than about 1 weight percent $C_2H_2$, from about 45 to about 55 weight percent $C_2H_4$, from about 25 to about 45 weight percent $C_2H_6$, and less than about 10 weight $C_{3+}$ material.

The quenched effluent in a line 310 is further cooled in a quench tower 311 where fuel oil and dilution steam are removed via a line 319. The effluent form the quench tower 311 is then passed to charge gas compressor 312 via a line 313 which operates to increase the pressure of the effluent to from about 350 psig to about 650 psig. Any of the known gas compressors may be employed in the practice of the present invention.

The compressed effluent in a line 314 is then sent to an acid gas removal and dehydration system 315. Acid gas is removed either by contact with a caustic or any of the amines as is known to those skilled in the art or both. Dehydration typically employs a water-absorbing molecular sieve capable of reducing the gas dew point to −200° F. or other means known to those skilled in the art. The effluent from system 315 is then directed via a line 317 to a $C_2$ hydrogenation reactor(s) 316 wherein the compressed effluent is contacted with a selective hydrogenation catalyst. Any hydrogenation catalyst well known to selectively hydrogenate acetylene can be employed in the hydrogenation reactor of the present invention. The Group VIII metal hydrogenation catalysts are the most commonly used and are presently preferred. The Group VIII metal hydrogenation catalysts are ordinarily associated with a support, such as alumina.

The catalysts are disclosed in the literature. See for example, La Hue et al., U.S. Pat. No. 3,679,762; Cosyns et al., U.S. Pat. No. 4,571,442; Cosyns et al., U.S. Pat. No. 4,347,392; Montgomery, U.S. Pat. No. 4,128,595; Cosyns et al., U.S. Pat. No. 5,059,732 and Liu et al., U.S. Pat. No. 4,762,956.

The hydrogenation conditions employed in the hydrogenation reactor(s) 316 according to the present invention can vary appreciably depending upon the compositional make-up of the stream being treated. Ordinarily, the temperature and pressure will be sufficient to complete the hydrogenation of substantially all of the $C_2$ acetylenes contained in the stream fed to the hydrogenation reactor 316. Generally, the hydrogenation process will be carried out at a temperature ranging from about 50° F. to about 400° F. and a pressure ranging from about 350 psia to about 600 psia.

Hydrogen is present in amounts at least sufficient to meet the stoichiometric requirements for converting acetylene into ethylene, and, generally, is in the range of about 1 to 100 mols of hydrogen per mol of acetylene. Reaction time can vary from about a few seconds to a few hours, and is generally in the range of from about 1 second to about 6 seconds. The process can be carried out employing the catalyst in a fixed bed(s) or other type of contacting means known to those skilled in the art.

The hydrogenated effluent in a line 318 is then further cooled against propylene refrigerant in a chilling train 320 producing a liquid stream 321 comprised primarily of $C_2$ and heavier material which is passed to a moderately low temperature demethanizer 328.

The vapor effluent 322 from the chilling train 320 is passed to a first serially connected dephlegmator 324 wherein the gas mixture is chilled to a temperature of from about −85° F. to about −120° F. to produce a vapor stream at least substantially free of $C_{3+}$ hydrocarbons issuing from the top of the first dephlegmator 324 in a line 330. The vapor effluent from the first dephlegmator 324 in the line 330 comprising mostly hydrogen, methane with some $C_2$ hydrocarbons is then passed to a second serially connected dephlegmator 332 wherein it is chilled to a temperature ranging from about −165° F. to about −235° F. A gaseous stream issuing from the top of the second dephlegmator 332 in a line 334 comprises hydrogen with some methane. The bottoms comprising substantially methane and ethylene are removed in a line 336.

The liquid issuing from the bottom of the first dephlegmator 324 in a line 326 comprised of $C_2$ and heavier hydrocarbons is low in hydrogen and methane and is passed to a moderately low temperature demethanizer 328 operating at a temperature of from about −20° F. to −80° F. and a pressure of from about 350 psia to about 550 psia to produce a vapor overhead in a line 338 that is substantially $C_{3+}$ free and a bottoms liquid in a line 344 substantially free of methane.

The substantially $C_{3+}$ free vapor in a line 338 and the stream 336 from the bottom of the second dephlegmator 332 are directed to a low temperature demethanizer 340 operating at a temperature ranging from about −100° F. to about −180° F. The vapor in a line 342 issuing from the top of the low temperature demethanizer 340 is substantially methane. In an especially preferred embodiment, the second demethanizer is also operated at a relatively low pressure, such as below about 175 psia and more preferably about 150 psia.

The liquid from the bottom of the moderately low temperature demethanizer 328 in a line 344 comprising from about 50 to about 65 weight percent ethylene and substantially free of methane is directed to a deethylenizer 346 operating at a pressure ranging from about 65 psia to about 400 psia. The overhead from the deethylenizer 346 in a line 348 comprising dilute ethylene is combined with the bottoms liquid substantially free of methane from the low temperature demethanizer 340 in a line 350 into a line 352 as a dilute ethylene product (at least 95.0 weight percent ethylene for a gas phase polyethylene polymerization reactor or at least about 85 weight percent for a solution phase polyethylene polymerization reactor) for feeding to an ethylene polymerization reactor 354.

As discussed above, the ethylene polymerization reactor 354 may comprise a gas phase reactor or a solution reactor. Where the concentration of the ethylene in the dilute ethylene feedstock 352 to the reactor 354 is below about 95% the solution polymerization technique is preferred in the practice of the present invention.

The product polyethylene is removed from the polymerization reactor 354 in a line 356. The purge from the reactor 354 is removed in a line 358 and is recycled either to the steam cracker via a line 360 in the case of a solution phase reaction, or preferably to the charge gas compressor 312 via a line 362 in the case of a gas phase reaction. Alternatively, return of the purge from the gas phase reactor to the cracking furnace is contemplated within the scope of the present invention with the expedient of employing a separating means (not shown), i.e., membrane technology or dephlegmation, to removed a substantial portion of the $N_2$, $H_2$ and $CH_4$ contained therein.

The liquid bottoms from the deethylenization tower 346 substantially free of ethylene is removed in a line 364 and passed to a deethanizer tower 366 wherein any remaining $C_2$ components or if desired C2 and $C_3$ components are removed in a line 370 and recycled to the steam cracker 304. The heavier components comprising $C_3$ and heavier compounds are removed for fuel in a line 368.

Figure 4:
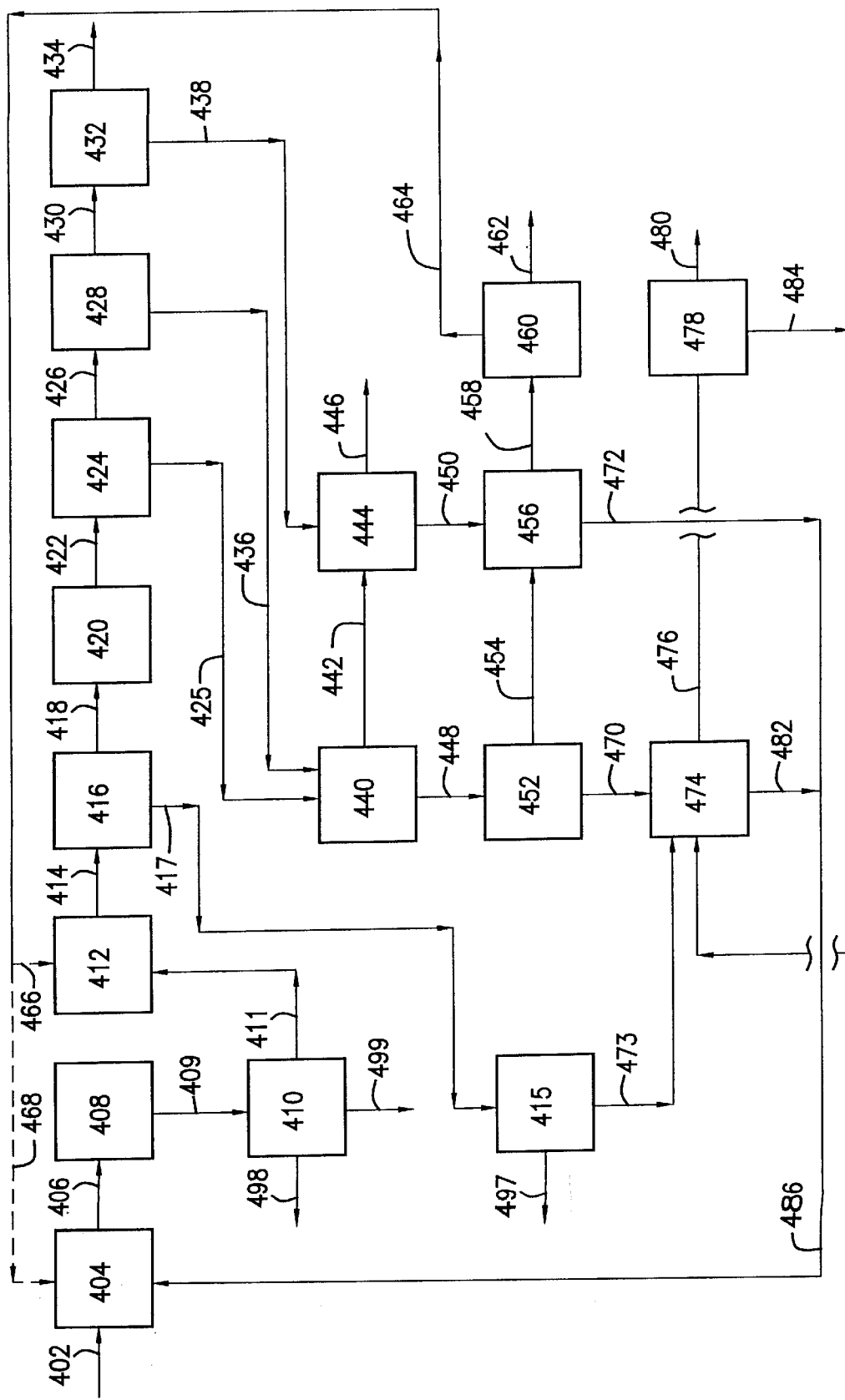
FIG. 4 depicts in flow chart form an embodiment of an integrated process for the production of polyethylene and polypropylene in accordance with the present invention.

Referring now to FIG. 4, a propane, butane, naphtha, gas oil, mixture thereof, or other liquid feedstock in a line 402 is fed to a steam cracker 404 and is cracked to produce minor amounts of hydrogen, acetylene, and fuel oil, and major amounts of methane, ethylene, ethane, propylene, propane and $C_4$ and heavier components in a line 406. The product stream is quenched in a quench boiler 408 to substantially stop the thermal reactions as described hereinabove. The quenched products in a line 409 are then passed to an oil and water quench system 410 to further cool the gas and remove fuel oil and dilution steam via lines 498 and 499, respectively. The cooled gas then passes to the charged gas compressor 412 via a line 411 which operates to increase the pressure of the effluent to from about 180 psig to about 300 psig.

The compressed products in a line 414 are fed to acid gas removal and dehydration systems (not shown) and then to a depropanizer 416. The depropanizer 416 preferably operates at relatively high pressures ranging from about 150 psia to about 300 psia and is equipped with a reboiler (not shown). The liquid bottoms fraction containing substantially all of the $C_4$ and heavier components and a large portion of the $C_3$ components is withdrawn from the high pressure depropanizer 416 through a line 417 and fed to the low pressure depropanizer 415. The low pressure depropanizer 415 separates the $C_3$ hydrocarbons overhead which feed the $C_3$ splitter 474 via a line 473 and a $C_{4+}$ bottoms stream 497.

The vapor overhead fraction from the high pressure depropanizer 416 in a line 418 comprising substantially the $C_3$ and lighter components is withdrawn and directed to an acetylene hydrogenation reactor 420. The acetylene hydrogenation reactor 420 operates as described above to hydrogenate substantially all of the acetylenes in the vapor to ethylene. Additionally some propynes and propadienes are converted to propylene.

The vapor from the hydrogenation reactor 420 in a line 422 is initially chilled in chilling train 424. The condensed effluent from the chilling train 424 is fed via a line 425 to the moderately low temperature demethanizer 440. The vapor from the chilling train 424 in a line 426 is passed to a first serially connected dephlegmator 428 wherein the gas mixture is chilled to a temperature of from about $-85°$ F. to about $-120°$ F. to produce a substantially $C_3$ free vapor issuing from the top of the first dephlegmator 428 in a line 430 comprising mostly hydrogen, methane and some $C_2$ hydrocarbons, which is then passed to a second serially connected dephlegmator 432 wherein it is chilled to a temperature ranging from about $-165°$ F. to about $-220°$ F. A gaseous stream issuing from the top of the second dephlegmator 432 in a line 434 comprises hydrogen and some methane.

The liquid issuing from the bottom of the first dephlegmator 428 in a line 436 comprising $C_2$ and heavier hydrocarbons and low methane and hydrogen is passed to a moderately low temperature demethanizer 440 operating at a temperature ranging from about $-20°$ F. to about $-80°$ F. and a pressure ranging from about 350 psia to about 550 psia to produce a vapor overhead in a line 442 at least substantially free of $C_3$ and heavier components and a bottoms liquid in a line 448 substantially free of methane.

The substantially free $C_{3+}$ vapor in a line 442 and the bottoms stream 438 from the second dephlegmator 432 are fed to a low temperature demethanizer 444 operating at a temperature ranging from about $-100°$ F. to about $-180°$ F. The vapor in a line 446 issuing from the top of the low temperature demethanizer 444 comprises substantially methane. In an especially preferred embodiment, the second demethanizer is also operated at a relatively low pressure, such as below about 175 psia and more preferably about 150 psia.

The liquid from the bottom of the moderately low temperature demethanizer 440 in a line 448 substantially free of methane is directed to a deethanizer 452 operating at a pressure ranging from about 300 psia to about 450 psia. The overhead from the deethanizer in a line 454 containing ethylene and ethane and the bottoms liquid in a line 450 from the low temperature demethanizer 444 are fed to a $C_2$ splitter 456 operating at a pressure ranging from about 100 psia to about 400 psia. The overhead from the $C_2$ splitter 456 comprising dilute ethylene is removed via a line 458 for feeding to an ethylene polymerization reactor 460. Optionally, where the polyethylene polymerization reactor 460 is a solution phase reactor, the $C_2$ splitter 456 may be eliminated altogether, and the bottoms liquid in a line 450 and the deethanizer overhead in a line 454 may be directly fed to the polyethylene polymerization reactor 460.

The ethylene polymerization reactor 460 may comprise a gas phase reactor or a solution reactor. Where the concentration of the ethylene in the feed to the reactor 460 is below about 95% the solution polymerization technique is preferred.

The product polyethylene is removed from the polymerization reactor 460 in a line 462. The purge from the reactor 460 is removed in a line 464 and is recycled either to the steam cracker via a line 468 in the case of a solution phase reaction, or preferably to the charge gas compressor 412 via a line 466 in the case of a gas phase reaction.

The liquid bottoms from the deethanizer 452 substantially free of $C_2$ hydrocarbons is removed in a line 470 and passed to a $C_3$ splitter 474 along with low pressure depropanizer 415 overhead via a line 473 wherein propane is removed in a line 482 and recycled to the steam cracker 404 via a line 486. The lighter fraction from the $C_3$ splitter 474 comprising dilute propylene, such as in an amount of at least about 85 weight percent, and more preferably about 95 weight percent, is removed via an overhead line 476 and fed to a propylene polymerization reactor 478.

The propylene polymerization reactor 478 typically comprises a polypropylene homopolymerization reactor (not shown) and an impact reactor (not shown) for copolymerizing the propylene homopolymer with minor amounts, i.e. from about 2 to about 15 weight percent ethylene, of ethylene.

Where the dilute propylene feed 476 has a propylene concentration of at least about 95 weight percent, either a bulk phase or gas phase homopolymerization reactor may be employed. The bulk phase polypropylene homopolymer reaction may employ any of the known reaction processes and preferably operates at a pressure ranging from about 400 psig to about 500 psig and a temperature ranging from about 120° F. to about 150° F. over Ziegler-Natta (Z/N) family catalysts or a single site metallocene family catalysts.

Alternatively, where the dilute propylene feed 476 has a propylene concentration of less than about 95 weight percent the gas phase homopolymerization reactor should be employed. The gas phase homopolymerization reactor may operate as is well known to those of ordinary skill in the art, typically at a pressure ranging from about 150 psig to about 400 psig, a temperature ranging from about 200° F. to about 400° F. over a Ziegler-Natta (Z/N) or a "single site" metallocene family catalyst.

The polypropylene homopolymer is then reacted with ethylene, in a concentration of from about 2 to about 15 weight percent, preferably from about 4 to about 10 weight percent, in an impact copolymerization reactor. Again this reaction is well known to those skilled in the art and any of the known operating parameters may be employed in the practice of the present invention. Typically, the impact copolymerization reactor operates at pressures ranging from about 150 psig to about 400 psig and temperatures ranging from about 200° F. to about 400° F. in the presence of a Ziegler-Natta (Z/N) or "single site" metallocene family catalyst.

The product polypropylene is removed from the polypropylene reactor 478 via a line 480. The purge from the polypropylene reactor is removed via a line 484 and is preferably recycled to the $C_3$ splitter 474.

The heavier components from the low pressure depropanizer 415 in a line 497 may optionally be further processed in a debutanizer (not shown) to remove the $C_4$ compounds for further processing into methyl tert butyl ether, polyisobutylene, butyl rubber or other petrochemicals.

Figure 5:
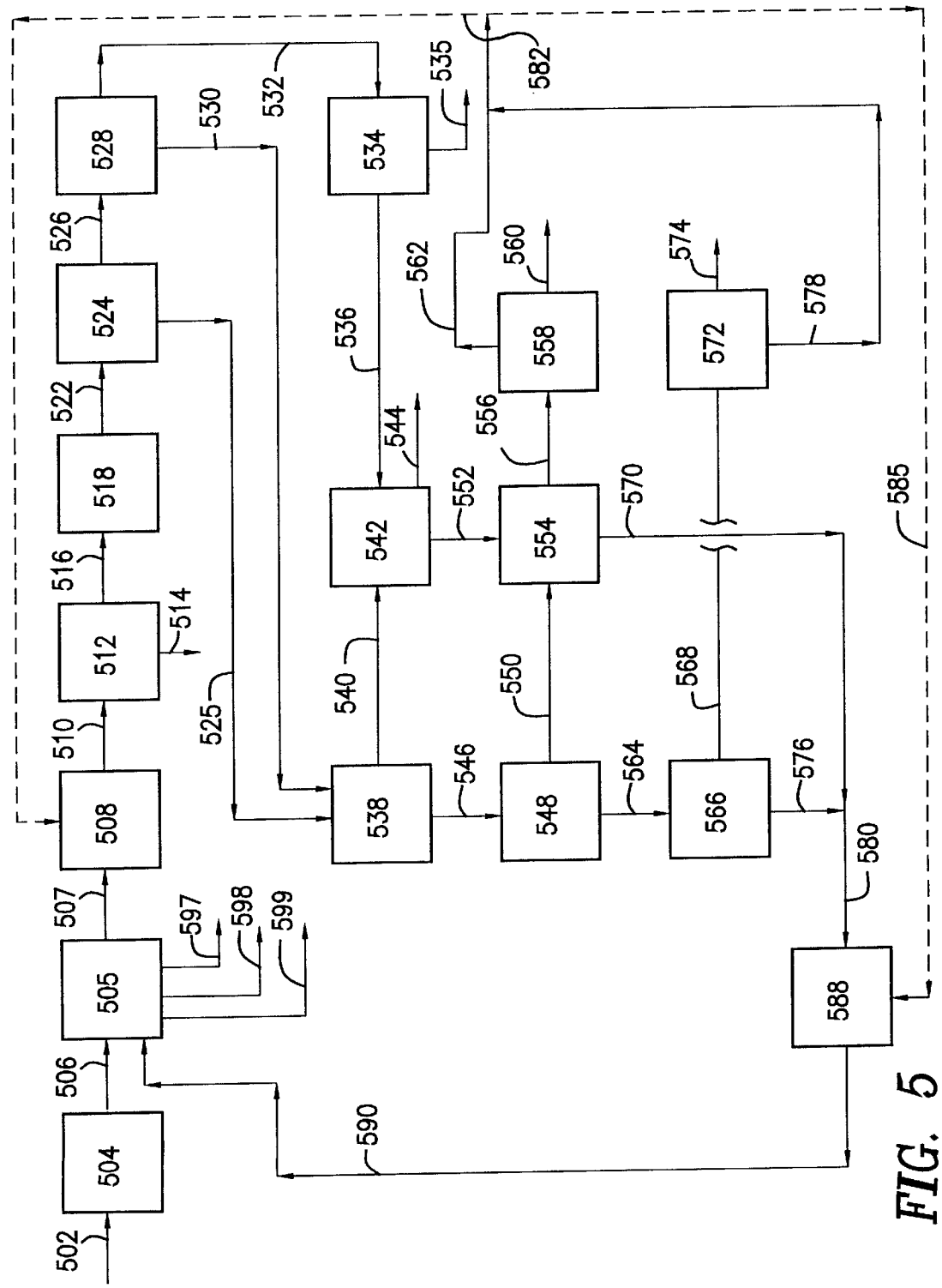
FIG. 5 depicts in flow chart form an embodiment of an integrated process for the production of olefin derivatives in accordance with the present invention.

In a further embodiment of the present invention, referring now to FIG. 5, a gas oil or other heavy feedstock in a line 502 is fed to a deep catalytic cracker 504 wherein the gas oil feedstock is cracked to produce hydrogen, methane, acetylene, butylenes and other $C_4$ hydrocarbons, gasoline and heavier components, ethylene, ethane, propylene and propane in a line 506. The products in a line 506 are then cooled in quench system 505 where the dilution steam, heavy fuel oil and other heavy liquid fractions are removed via lines 597, 598 and 599, respectively. The remaining light gases are then passed to charge gas compressor 508 via a line 507 which operates to increase the pressure of the effluent to from about 350 psig to about 520 psig.

The compressed products in a line 510 are then fed to an acid gas removal system and dehydration system (not shown) and then to a depropanizer 512. The depropanizer 512 preferably operates at relatively high pressures ranging from 150 psia to 300 psia and is equipped with a reboiler (not shown).

The liquid bottoms fraction containing substantially all of the $C_4$ hydrocarbons, gasoline and heavier components is withdrawn from the high pressure depropanizer 512 through a line 514 for further processing such as through a debutanizer to remove the $C_4$ hydrocarbons and further rectification units to recover gasoline as is known to those skilled in the art. Portions of the heavier components may also be recycled to the deep catalytic cracker for further cracking. The vapor overhead fraction from the depropanizer 512 in a line 516 comprising substantially the $C_3$ and lighter components is withdrawn and directed to an acetylene hydrogenation reactor 518.

The acetylene hydrogenation reactor 518 operates as described above to hydrogenate substantially all of the acetylenes in the vapor to ethylene. Additionally propynes and propadienes are converted to propylene.

The vapor in a line 522 is then initially chilled and heavy liquids removed in drum 524. The vapor from drum 524 is then passed to a first serially connected dephlegmator 528 wherein the gas mixture is chilled to a temperature of from about −85° F. to about −120° F. to remove substantially all of the hydrogen from the gaseous mixture. The vapor issuing from the top of the first dephlegmator 528 in a line 532 comprising mostly hydrogen, methane and $C_2$'s is then passed to a second serially connected dephlegmator 534 wherein it is chilled to a temperature of from about −165 to about −200° F. A gaseous stream issuing from the top of the second dephlegmator 534 in a line 535 comprises hydrogen and some methane.

The liquid issuing from the bottom of the first dephlegmator 528 and from the chilling train drum 524 in lines 530 and 525, respectively, comprising $C_2$ and $C_3$ hydrocarbons and low methane and hydrogen is passed to a moderately low temperature demethanizer 538 operating at a temperature ranging from about −20° F. to about −80° F. and a pressure ranging from about 350 psia to about 550 psia to produce a vapor overhead in a line 540 at least substantially free of $C_{3+}$ hydrocarbons and a bottoms liquid in a line 546 substantially free of methane.

The substantially $C_{3+}$ free vapor in a line 540 and the bottoms from the second dephlegmator 534 in a line 536 are fed to a low temperature demethanizer 542 operating at a temperature ranging from about −100° F. to about −180° F. The vapor in a line 544 issuing from the top of the low temperature demethanizer 542 comprises substantially pure methane. In an especially preferred embodiment, the second demethanizer is also operated at a relatively low pressure, such as below about 175 psia and more preferably about 150 psia.

The liquid from the bottom of the moderately low temperature demethanizer 538 in a line 546 substantially free of methane is directed to a deethanizer 548 operating at a pressure ranging from about 300 psia to about 450 psia. The overhead from the deethanizer in a line 550 containing ethylene and ethane is combined with the bottoms liquid in a line 552 from the low temperature demethanizer 542 to a $C_2$ splitter 554 operating at a pressure ranging from about 100 psia to about 400 psia. The overhead from the $C_2$ splitter 554 comprises a dilute ethylene feedstock in a line 556 for feeding to an ethylene derivative reactor 558.

The ethylene derivative reactor 558 may comprise a reactor for producing any ethylene derivative petrochemical in a line 560 as described hereinabove. For example the ethylene derivative reactor may comprise a reactor for the production of polyethylene (see FIG. 4), ethylene dichloride, vinyl chloride monomer, ethyl benzene, styrene, acetaldehyde, vinyl acetate, acrylic acid and propionaldehyde. Optionally, the dilute ethylene feedstock in a line 556 may be in direct communication with one or more ethylene derivative reactors 558 in order to produce more than one ethylene derivative petrochemical product.

The purge from the ethylene derivative reactor 558 is removed in a line 562 and is recycled to a steam cracking reactor 588 via a line 585 or to the charge gas compressor 508 via a line 582 dependent upon the particular ethylene derivative reactor employed and the reaction by-products contained in the purge stream 562.

The liquid bottoms from the $C_2$ splitter 554 in a line 570 comprising substantially ethane is recycled to a steam cracking reactor 588 via a recycle line 580. The effluent from the steam cracking reactor can be fed to the quench system 505 via a line 590.

The liquid bottoms from the deethanizer 548 substantially free of $C_2$ hydrocarbons are removed in a line 564 and passed to a $C_3$ splitter 566 wherein propane is removed in a line 576 and recycled to the steam cracking reactor 588 via a recycle line 580. The lighter fraction from the $C_3$ splitter 566 comprising a dilute propylene feedstock is removed via an overhead line 568 and fed to a propylene derivative reactor 572.

The propylene derivative reactor 572 may comprise a reactor for producing a propylene derivative petrochemical in a line 574 as described hereinabove. For example the propylene derivative reactor may comprise a reactor for the production of polypropylene (see FIG. 4), acrylonitrile, propylene oxide, isopropanol, acrolein, butyraldehyde, allyl chloride, isopropyl acrylate, isopropyl acetate, allyl acetate and cumene. Optionally, the dilute propylene feedstock in a line 568 may be in direct communication with one or more propylene derivative reactors 572 in order to produce more than one propylene derivative petrochemical product.

The purge from the propylene derivative reactor 572 is removed in a line 578 and is recycled either via a line 582 to the charge gas compressor 508 or to the steam cracking reactor 588 via a line 585.

In many of the process sequences of the present invention, substantial amounts of $C_4$ hydrocarbons are also produced. The majority of the $C_4$ compounds are removed in the depropanizer along with other heavier hydrocarbons. The $C_4$ hydrocarbons can be recovered from the depropanizer bottoms in any conventional manner, typically from the overhead of a debutanizer tower as is well known to those skilled in the art. The $C_4$ hydrocarbons recovered from the debutanizer typically comprises all of the $C_4$ isomers, n-butane, isobutane, 1-butene, cis-2-butene, trans-2-butene, ethyl acetylene, vinyl acetylene, 1,3-butadiene, 1,2-butadiene, and isobutylene, as well as minor amounts of $C_3$ and $C_5$ hydrocarbons.

The present invention also contemplates the further processing of the mixed $C_4$ compounds into petrochemical products. In an especially preferred embodiment, the mixed $C_4$ compounds may be further processed by steps including hydrogenation, extractive distillation and skeletal isomerization in combination with a methyl tert butyl ether synthesis step, a polyisobutylene polymerization step, or a butyl rubber producing step. See generally, Rubin et al., U.S. Pat. No. 5,382,707.

Figure 6A:
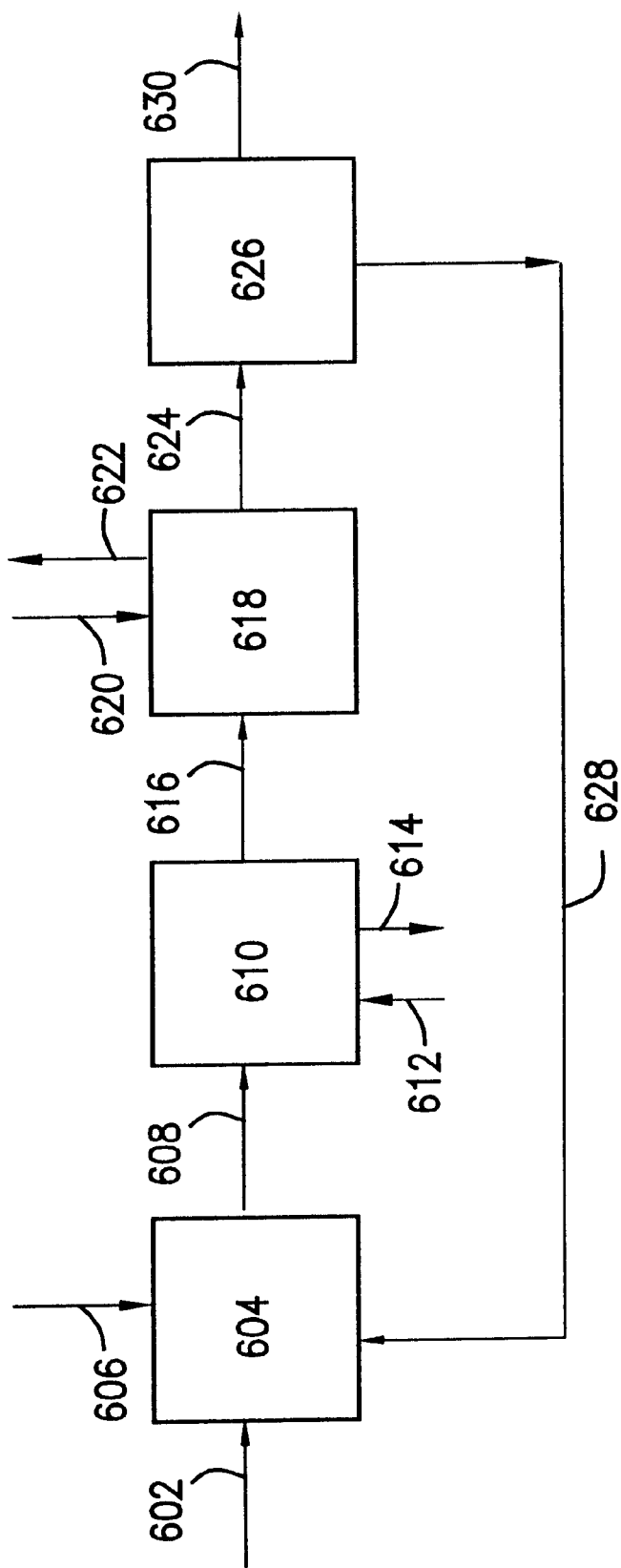
FIGS. 6A, 6B and 6C depict in flow chart form $C_4$ hydrocarbon downstream processing embodiments useful in the practice of the integrated process of the present invention.

Referring to FIG. 6A, in this manner the mixture of $C_4$ compounds from the overhead of a debutanizer (not shown) in a line 602 is first fed to a hydroisomerization unit 604. Alternatively, the hydroisomerization unit can comprise any butadiene hydrogenation unit known to those of ordinary skill in the art which converts butadiene to butenes, such as a selective hydrogenation unit. Preferred is a hydroisomerization unit which in addition to converting butadiene to butenes also isomerizes at least a portion of the butene-1 component to the butene-2 components. The hydroisomerization unit 604 is fed with hydrogen by a line 606. The $C_4$ compounds in line 602 are typically a mixture of all of the $C_4$ isomers (acetylenes, dienes, olefins and paraffins), and small quantities of $C_3$ and $C_5$ hydrocarbons.

In the hydroisomerization unit 604, most of the acetylenes and dienes are catalytically converted to butenes and most of the 1-butene is catalytically converted to the 2-butenes, i.e., cis-2-butene and trans-2-butene, in the presence of hydrogen.

Hydroisomerization is a process which is well known to those of ordinary skill in the art and any particular hydroisomerization process may be employed. Typically, the hydroisomerization step is carried out in the presence of a catalyst comprising at least one hydrogenating metal and a moderately acidic carrier. A preferred catalyst can comprise a Group VIII metal, such as platinum, palladium and/or nickel, on a microporous crystalline silicate, such as a mordenite with a surface area of from 100 to 800 $m^2/g$.

Suitable hydroisomerization conditions may include a temperature ranging from about 100° F. to about 750° F., a pressure ranging from about 1 bar to about 100 bar and a space velocity ranging from about 0.5 to about 20 kg hydrocarbon feed/kg catalyst hour. Preferred conditions are a mixed phase process at a temperature ranging from about 100° F. to about 1400° F., a pressure ranging from about 145 psia to about 580 psia and a space velocity ranging from about 1 to about 15 lb feed/lb catalyst hour. See, e.g., Grandvallet et al., U.S. Pat. No. 5,023,389.

The effluent stream 608 from the hydroisomerization unit 604 substantially comprising isobutylene, cis-2-butene, trans-2-butene, isobutane, n-butane, unconverted 1-butene and $C_3$ and $C_5$ components is then directed to an MTBE synthesis unit 610.

The synthesis of methyl tertiary butyl ether (MTBE) from isobutylene and methanol, supplied via a line 612, is a process which is well known to those of ordinary skill in the art and any particular synthesis process may be employed in the practice of the present invention. The general reaction scheme is set forth below.

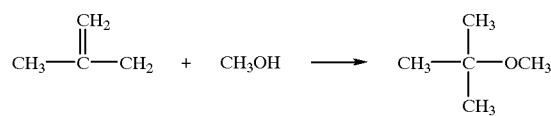

Typically, the synthesis step is carried out at mild temperatures, in the liquid phase, in the presence of a sulfonated polystyrene resin. See, Hatch and Matar, "From Hydrocarbons to Petrochemicals," Gulf Publishing Co., 1981, pp. 128–29.

The reaction usually employs an acid type ion exchange resin, such as a high molecular weight carbonaceous material containing sulfonate groups —$SO_3H$. Sulfonated resins of various types are available such as the sulfonated coals, phenol formaldehyde resins reacted with sulfuric acid, sulfonated resinous polymers of cumarone-indene with cyclopentadiene, strongly acidic cationic exchange resins such as sulfonated divinylbenzene polystyrene copolymers, and others, under various commercial names. The catalyst can be employed in a particulate solid form with sizes ranging from about 10 to about 50 U.S. sieve employing from about 0.5 to about 50 percent dry weight of catalyst relative to liquid content of the reactor. A fixed bed of particulate solid ion exchange resin catalyst, e.g., such as Amberlyst 15 from Rohm & Haas Co., or Dowex M31 or M32 from Dow Chemical Co., may be employed. The same catalyst may also be employed in tubular reactors or supported in bags or other devices which permit catalytic distillation to be practiced.

The reaction of the isobutylene with methanol can be carried out under any suitable reaction conditions. The mole ratio of methanol to isobutylene generally is in the range of from about 0.05 to about 10, preferably from about 0.1 to about 5, and still more usually about 1 to 1, at a temperature in the range of from about 100° F. to about 250° F., employing a pressure sufficient to maintain the reactants substantially in the liquid state, typically in the range of from about 80 psig to about 400 psig. The liquid hourly space velocity, volume of feed per volume of catalyst per hour, is preferably from about 0.5 to about 10.

More specific processes of MTBE synthesis are described in Childs, U.S. Pat. No. 4,440,963, Wentzheimer et al., U.S. Pat. No. 4,198,530, Masilamani et al., U.S. Pat. No. 4,792,639, Smith, Jr. et al., U.S. Pat. No. 4,950,803, Lee, U.S. Pat. No. 3,946,450 and Leum et al., U.S. Pat. No. 2,480,940.

The resultant product MTBE, along with the $C_5$ and heavier components, are withdrawn from the MTBE unit through a line 614 by fractionation, as is well known to those skilled in the art.

The remaining components of the MTBE synthesis feed, the cis-2-butene, trans-2-butene, isobutane, n-butane, unconverted 1-butene and $C_3$ components are then directed through a line 616 to a paraffin/olefin separation unit. The paraffin/olefin separation can be carried out by a wide variety of separation processes known to those skilled in the art, including, but not limited to, extractive distillation and/or molecular sieve separation. Particularly suitable for use in the practice of the present invention is an extractive distillation unit 618 to remove paraffins and $C_3$ components.

Extractive distillation is a well known process, and has been employed in the past to separate butadiene from $C_4$ feedstreams, as well as other separations such as separating MTBE from cyclopentane. See, e.g., Berg, U.S. Pat. No. 4,661,209. Extractive distillation generally refers to processes where a higher boiling selective solvent is added to the separation feed mixture to alter the relative volatilities of the components in the feed mixture. See, generally, Perry and Chilton, "Chemical Engineers' Handbook," McGraw Hill, 5th ed., 1973, pp. 13–43 to 13–48.

A wide variety of solvents may be employed in the extractive distillation step of the present invention, including, but not limited to, tetra-hydrofuran, diethyl ketone, diethyl carbonate, methyl ethyl ketone, pentanedione, cyclopentanone, acetone, butyronitrile, acetyl piperidine, acetophenone, pyridine, diethyl oxalate, propionitrile, dimethyl acetamide, n-methyl pyrrolidone, acetonyl acetone, tetrahydrofurfuryl alcohol, dimethyl sulfolane, dimethyl cyanamide, methyl carbitol, dimethyl formamide, methyl cellosolve, furfural, acetonitrile, ethylene chlorhydrin, gamma-butyrolactone, methanol, beta-chloropropionitrile, pyrrolidone, propylene carbonate, nitromethane, ethylene diamine and mixtures of any of the foregoing. Especially preferred is acetonitrile. Further, these solvents may also be employed with a water diluent.

The solvent, in a line 620, is introduced near the top of the extractive distillation column or tower (not shown), usually a few plates from the top, and flows downward until it reaches the stillpot or reboiler. Its presence on each plate of the distillation column alters the relative volatility of the close boiling compounds to make the separation on each plate greater than would be possible without the solvent and thus requires either fewer plates to effect the same degree of separation, makes possible a greater degree of separation with the same number of plates, or makes possible separations which could not be achieved with conventional distillation.

The lighter compounds, $C_3$ and lighter boiling hydrocarbons, as well as the $C_4$ paraffins, isobutane and n-butane, are thereby removed from the top of the extractive distillation unit through a line 622. The bottoms from the extractive distillation are directed to a stripper (not shown) wherein the cis-2-butene, trans-2-butene and unconverted 1-butene are recovered from the overhead of the stripper, withdrawn through a line 624 and fed to the skeletal isomerization unit 626.

Skeletal isomerization is a process by which the normal butenes, cis-2-butene, trans-2-butene and 1-butene, are converted to isobutylene. Skeletal isomerization of olefins is known to be conducted by contacting unbranched olefins with acidic catalysts at pressures near atmospheric and temperatures ranging from about 600° F. to about 1100° F. The isomerization of olefins is well known to be limited by the thermodynamic equilibrium of reacting species. Useful catalysts and processes are described in the patent literature, inter alia, Smith, Jr., U.S. Pat. No. 4,482,775, Sun, U.S. Pat. No. 4,778,943, Schwerdtel et al., U.S. Pat. No. 4,548,913, Del Rossi et al., U.S. Pat. No. 5,107,047 and Chih-Cheng, et al., EP 0 508 008.

Accordingly, in the skeletal isomerization reactor 626 a portion of the normal butenes are converted to isobutylene with a small amount of light and heavy hydrocarbon by-products (gasoline) and the effluent from the skeletal isomerization unit is recycled in a line 628 to the hydroisomerization reactor 604 wherein the butene-1 component can be further isomerized to butene-2 components. Alternatively, the skeletal isomerization effluent 628 can be directly recycled to the MTBE synthesis unit for conversion of the isobutylene to MTBE product. The heavy hydrocarbon by-products (gasoline) from the skeletal isomerization unit are withdrawn through a line 630.

When a relatively minor quantity of heavy hydrocarbon (gasoline) by-product is produced in the skeletal isomerization unit the heavy hydrocarbon takeoff stream 630 can be omitted and the heavy hydrocarbon can be recycled with the rest of the effluent from the skeletal isomerization unit in a stream 628 to the hydroisomerization or MTBE synthesis unit where it can be purged or removed from the process with the methyl tertiary butyl ether product stream 614.

Alternatively, the $C_4$ processing step of FIG. 6A can be operated to produce polyisobutylene, butyl rubber or methyl methacrylate or any other petrochemicals employing isobutylene as a reactant. These are exemplified in FIGS. 6B and 6C wherein like reference numerals with a ' or a " thereafter employed to represent similar process steps as discussed hereinabove with regard to FIG. 6A.

Figure 6B:
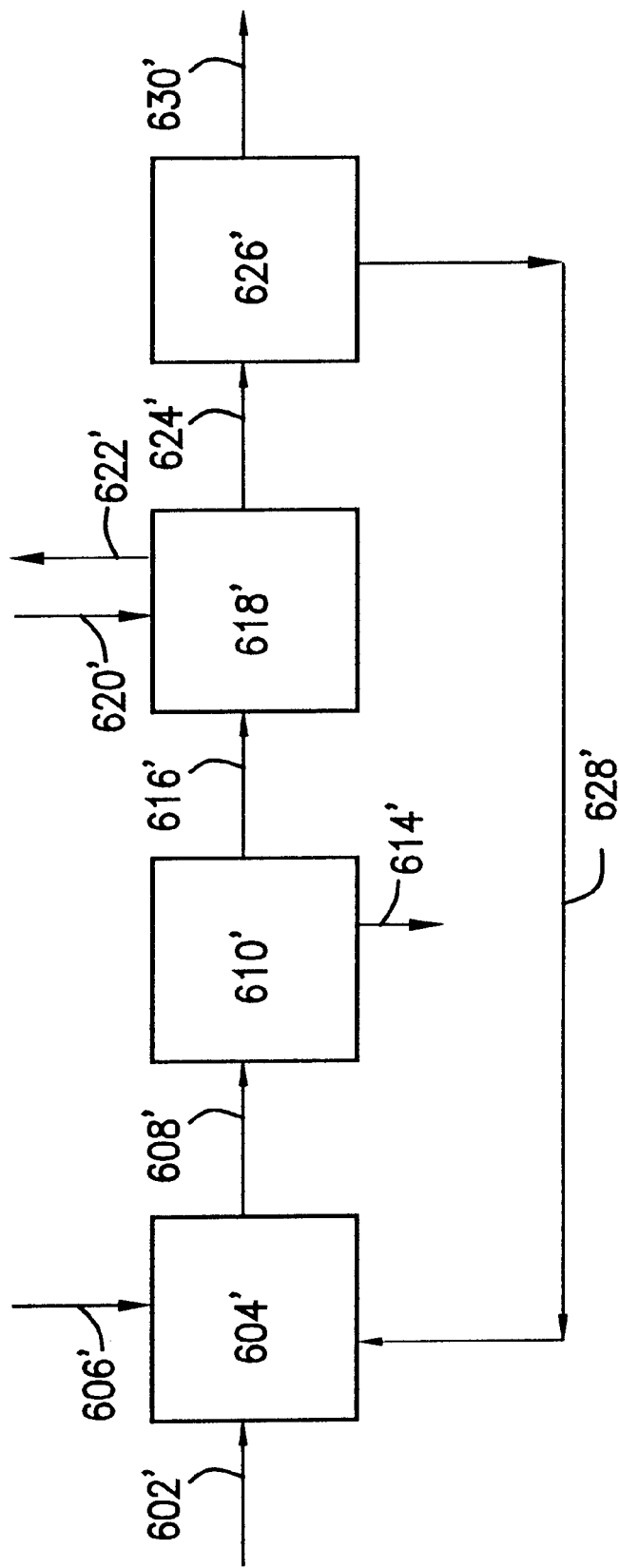

In the case of polyisobutylene, referring to FIG. 6B, a polymerization reactor 610' is employed in place of the methyl tert butyl reactor 610. The polymerization reaction process may be any known to those of ordinary skill in the art to effect polymerization of isobutylene to polyisobutylene, such as the Fina process. Typical operating parameters are temperatures of from about 35° F. to about 100° F. and a pressure ranging from about 10 psig to about 150 psig. See, e.g., Eaton, U.S. Pat. No. 5,068,490; Chen et al., U.S. Pat. No. 4,558,170; McCaulay, U.S. Pat. No. 4,288,649; and Johnson et al., United Kingdom Patent No. GB 1,378,330.

Figure 6C:
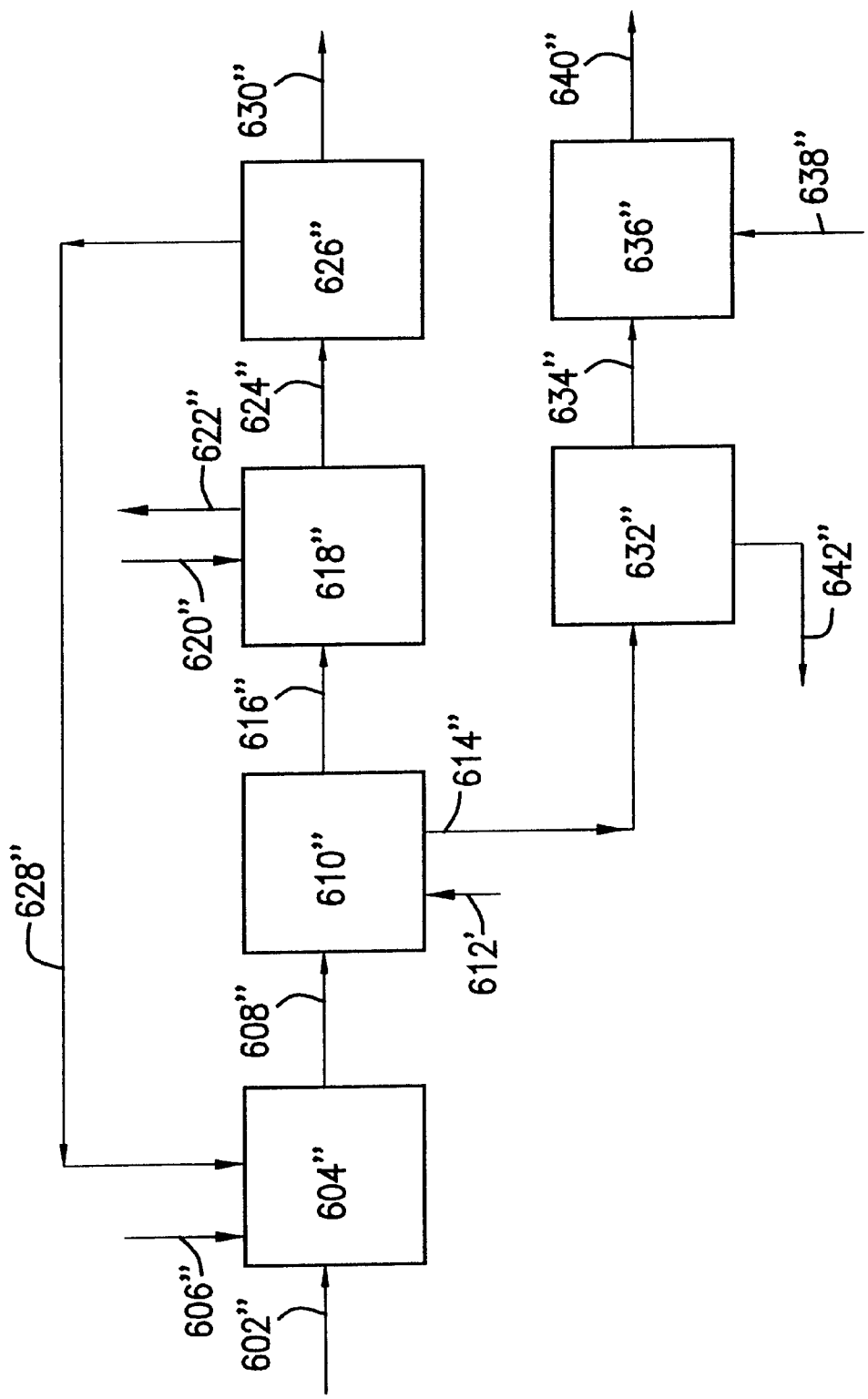

Referring to FIG. 6C in the case of butyl rubber, the hydroisomerized $C_4$ stream in a line 608" is fed to a methyl tert butyl ether reactor 610" which is fed with methanol via a line 612". Optionally, a solvent extractor for selectively removing isobutylene may be employed as separator unit 610". The product methyl tert butyl ether in a line 614" is then fed to a decomposition reactor 632" wherein the methyl tertiary butyl ether is decomposed into methanol and isobutylene. The methanol is removed in a line 642" and may be recycled to the methyl tertiary butyl ether reactor via a line 612".

The isobutylene in a line 634" is then fed to butyl rubber reactor 636" wherein it is contacted with isoprene via a line 638". Butyl rubber is produced by the cationic copolymerization of isobutylene in amounts ranging from about 95 to about 99, preferably about 97.5 weight percent and isoprene in amounts ranging from about 5 to about 1, preferably about 2.5 weight percent. The polymerization is typically carried out a low temperatures, on the order of from about −30° F. to about −100° F. in the presence of a Lewis acid catalyst such as $AlCl_3$ and a very small amount of water as a cocatalyst. See generally, Hatch and Matar, "From Hydrocarbons to Petrochemicals," 1981, pp. 212–213. The butyl rubber product is then removed in a product line 640".

Alternatively, the isobutylene in line 634" may be reacted to produce methyl methacrylate or other petrochemicals employing reactor 636". In the case of methyl methacrylate, the isobutylene may be catalytically oxidized over a complex molybdenum oxide catalyst at temperatures ranging from about 660° F. to about 850° F. and from about 15 psig to about 25 psig to produce methacrolein. The methacrolein is then oxidized over a molybdenum catalyst at temperatures of from about 480° F. to about 670° F. and from about 15 psig to about 25 psig to produce methacrylic acid.

The methacrylic acid is then esterified with methanol to produce methyl methacrylate at conditions well known to those skilled in the art. See, Kida et al., U.S. Pat. No. 4,343,959. See also, Hatch and Matar, "From Hydrocarbons to Petrochemicals", 1981, pp. 127–130; and Shimizu et al., "Methyl methacrylate from isobutylene via vapor-phase catalytic oxidation," Energy Proj., 8(3), 1988, pp. 169–172.

In another embodiment the present invention also provides for the debottlenecking of an existing olefins facility.

Olefins units are frequently limited in capacity either by the availability of refrigeration or limitations in the ethylene and/or propylene fractionation equipment or both. This invention, coupled with the expansion techniques of the Advanced Recovery System (ARS) (U.S. Pat. Nos. 4,900,347; 5,035,732 and 5,414,170) can significantly increase the economic expandability of existing olefins facilities.

Figure 7:
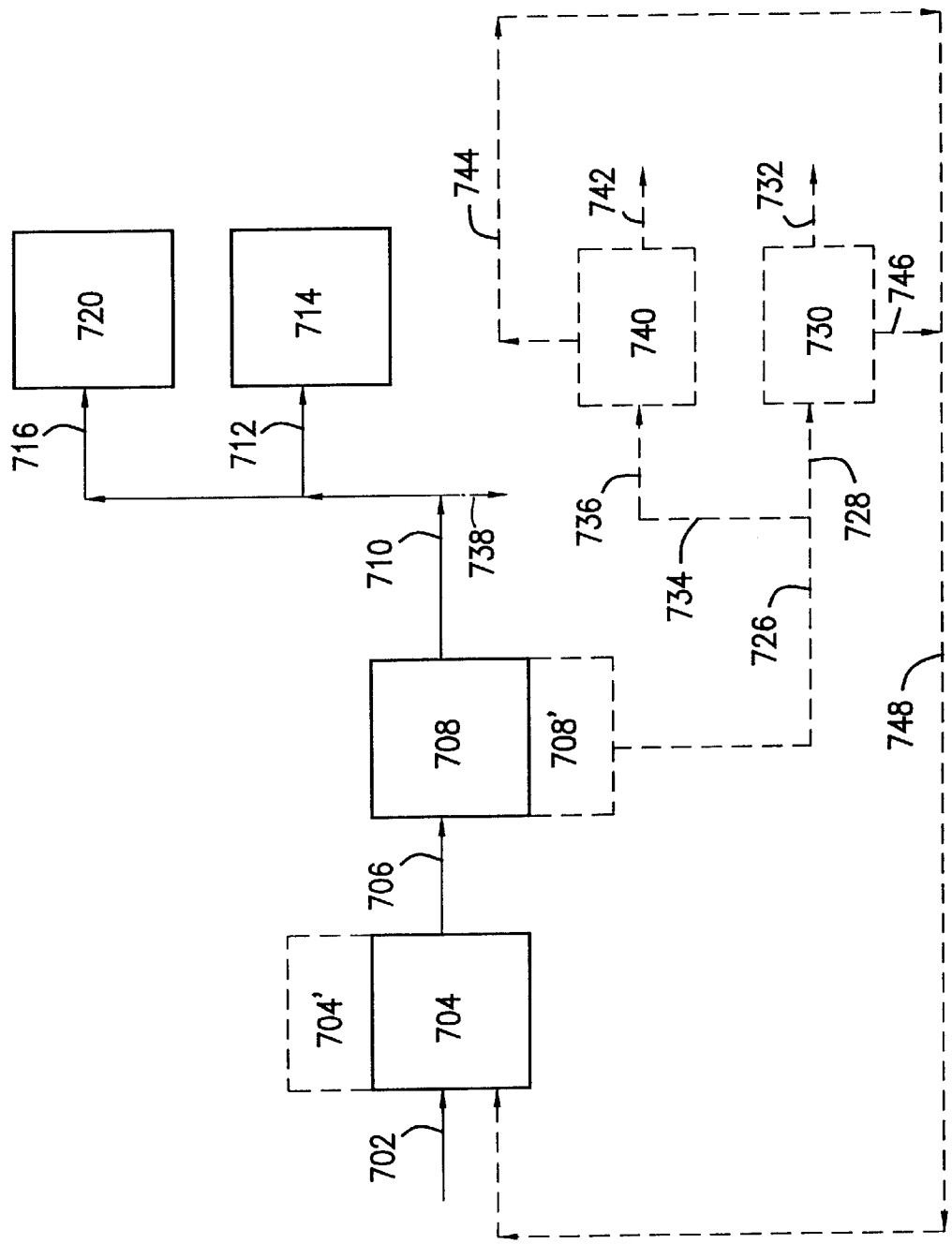
FIG. 7 depicts in flow chart form a debottlenecking embodiment of the present invention.

In FIG. 7, the solid lines could represent a process sequence for the production of gas phase polyethylene and high pressure low density polyethylene with polymer grade ethylene. The process represented by the solid lines of FIG. 7 does not exist in the prior art in one facility and is not integrated. The cracking, purification and polymerization processes conventionally take place in separate facilities. The flow chart is merely provided to simplify the explanation of the means of debottlenecking provided by the present invention.

The dotted lines represent an example of a means for debottlenecking such a process sequence in accordance with the present invention.

In the typical process sequence, an ethane feedstock in a line 702 is steam cracked in a cracking furnace 704 to produce ethylene and other hydrocarbon byproducts. The effluent from the cracking furnace 704 in a line 706 is then fed to a purification system 708 wherein the effluent is subjected to various rectification steps to produce a polymer grade ethylene product at about 99.9% purity in a line 710.

The highly pure ethylene in a line 710 is then fed to a facility for polymerization to polyethylene by solution or gas phase polymerization in a reactor 714 and high pressure low density polyethylene in a reactor 720 via lines 712 and 716 respectively, as is well known to those skilled in the art.

This process sequence can be conveniently revamped to provide a debottlenecked integrated process by adding additional furnace capacity 704' and by modifying the purification system 708 to produce one ethylene product at the current purity and one as a dilute stream in a line 726. The dilute ethylene feedstock can then be employed in a variety of ethylene derivative processes such as feeding dilute ethylene in a line 728 to a solution phase polyethylene reactor 730 to produce polyethylene in a line 732, and feeding a dilute ethylene feedstock via a line 734 to a reactor 740 to produce ethyl benzene or other ethylene derivative in a line 742.

Still further, a portion of the highly pure ethylene in a line 710 may optionally be directed to the polyethylene polymerization reactor 730, ethylene derivative reactor 740 or both via a line 738. The purges from the downstream derivative reactors 730 and 740 in lines 746 and 744, respectively, can then be recycled to the cracking reactor 704 via a line 748 to provide the integrated process of the present invention.

Many variations of the present invention will suggest themselves to those skilled in the art in light of the above-detailed description. All such obvious modifications are within the full intended scope of the appended claims.

All of the above-reference patents, patent applications and publications are hereby incorporated by reference in their entirety.

We claim:

1. An integrated process for the production of an olefin derivative product from a hydrocarbon feedstock in a grass-roots plant or expansion of an existing facility comprising the steps of:
   (a) cracking a hydrocarbon feedstock to produce a cracked product comprising a cracked gas comprising ethylene, or propylene or both and optionally one or more of ethane, acetylenes, methane, hydrogen, propane, and $C_4$ and heavier components;
   (b) recovering a dilute ethylene stream, a dilute propylene stream or both from said cracked gas;
   (c) processing either
      (i) said dilute ethylene stream to produce at least one ethylene derivative product and byproduct, or
      (ii) said dilute propylene stream to produce at least one propylene derivative product and byproduct, or
      (iii) both; and
   (d) recycling the by-product streams from said processing step (c) to the cracking step (a).

2. A process as defined in claim 1 wherein said hydrocarbon feedstock is selected from the group consisting of ethane, propane, butane, naphtha, gas condensates, raffinate, atmospheric gas oil, vacuum gas oil, natural gas liquids, distillate, crude oil, crude resid and mixtures of any of the foregoing.

3. A process as defined in claim 1 wherein said cracking step comprises a steam cracking process comprising the steps of:
   (i) preheating the feedstock to a temperature of from about 1000° F. to about 1300° F. in a convection zone of a thermal cracking furnace;
   (ii) mixing steam with said hydrocarbon feedstock in said convection zone to produce a vapor feedstock/steam mixture;
   (iii) thermally cracking said feedstock by passing the feedstock/steam mixture through at least one process coil in a radiant zone of said thermal cracking furnace, whereby said feedstock/steam mixture is heated to an outlet temperature of from about 1350° F. to about 1650° F. and cracked in said radiant zone to produce a cracked product gas stream comprising one or more of ethylene, ethane, acetylenes, methane, hydrogen, propane, propylene and $C_4$ and heavier components.

4. A process as defined in claim 3 which further comprises quenching the cracked product stream from said steam cracking step to produce a quenched product stream.

5. A process as defined in claim 1 wherein said cracking step comprises a non-catalytic thermal regenerative cracking process comprising the steps of:
   (a) contacting said feedstock with hot non-catalytic particulate solids;
   (b) thermally cracking said hydrocarbon feedstock at a temperature ranging from about 1200° F. to about 1600° F. with heat provided by said hot non-catalytic particulate solids to produce a cracked product gas comprising one or more of ethylene, ethane, acetylenes, methane, hydrogen, propane, propylene and $C_4$ and heavier components and coked solid particulates;
   (c) separating said cracked product gas from said coked solid particulates;
   (d) regenerating said coked particulate solids by burning off the coke therefrom and thereby heating the particulate solids; and
   (e) recycling said heated regenerated particulate solids to the contacting step (a).

6. A process as defined in claim 1 wherein said cracking step comprises a fluid catalytic cracking process comprising the steps of:
   (a) contacting said feedstock with catalytic particles;
   (b) catalytically cracking said hydrocarbon feedstock at a temperature ranging from about 800° F. to about 1300° F. with heat provided by said hot catalytic particles to produce a cracked product gas comprising one or more of ethylene, ethane, acetylenes, methane, hydrogen, propane, propylene and $C_4$ and heavier components and coked catalytic particles;

(c) separating said cracked product gas from said coked catalytic particles;

(d) regenerating said coked catalytic particles by burning off the coke therefrom and thereby heating the catalytic particles; and (e) recycling said heated regenerated catalytic particles to the contacting step (a).

7. A process as defined in claim 1 wherein said cracking step comprises a deep catalytic cracking process comprising the steps of:

(a) contacting a hydrocarbon feedstock with a solid acidic catalyst selected from the group consisting of pentasil shape selective molecular sieves, ultrastable hydrogen Y sieves and a mixture of ultrastable hydrogen Y sieves and pentasil shape selective molecular sieves in a fluidized or moving bed or dense phase transfer line reactor;

(b) cracking said hydrocarbon feedstock in the presence of steam at a temperature ranging from about 925° F. to about 1350° F. and a pressure ranging from about 20 psia to about 45 psia at a weight hourly space velocity ranging from about 0.2 to about 20 $hr^{-1}$, a catalyst-to-oil ratio of from about 2 to about 12 and a steam-to-feedstock ratio of from about 0.01 to about 0.5:1 by weight to produce a cracked gas and coked catalytic particles;

(c) separating said cracked product gas from said coked catalytic particles;

(d) regenerating said coked catalytic particles by burning off the coke therefrom and thereby heating the catalytic particles; and (e) recycling said heated catalytic particles to the contacting step (a).

8. A process as defined in claim 1 wherein said cracked gas comprises a mixed olefin stream and said recovery step (b) comprises:

(I) compressing said mixed olefin stream to a pressure of from about 350 psig to about 650 psig to produce a compressed mixed olefin stream;

(II) removing acid gas from said compressed mixed olefin stream with a caustic or amine acid gas removal system;

(III) drying said acid gas removed mixed olefin stream over water-absorbing molecular sieve to a dew point of about −200° F. to produce a dried mixed olefin stream;

(IV) selectively hydrogenating the acetylenes in said dried mixed olefin stream to produce a hydrogenated mixed olefin stream;

(V) dephlegmating said dried mixed olefin stream to produce a first vapor stream substantially free of $C_{3+}$ hydrocarbons and a first liquid stream rich in $C_{2+}$ hydrocarbons;

(VI) further dephlegmating said first vapor stream to produce a second vapor stream comprising hydrogen and methane, and a second liquid stream rich in methane and ethylene;

(VII) separating said first liquid stream in a moderately low temperature demethanizer to produce a third vapor stream substantially free of $C_{3+}$ hydrocarbons and a third liquid stream rich in $C_{2+}$ hydrocarbons;

(VIII) passing said second liquid stream and said third vapor stream to a low temperature demethanizer to produce a fourth vapor stream comprising substantially methane and a fourth liquid stream comprising dilute ethylene;

(IX) separating said third liquid stream in a deethylenization tower to produce an overhead stream comprising dilute ethylene and a fifth liquid stream substantially free of ethylene;

(X) recovering said fourth liquid stream and said deethylenization overhead stream as said dilute ethylene stream;

(XI) separating said fifth liquid stream in a deethanizer tower to produce a sixth liquid stream comprising $C_3$ and heavier components and a fifth gaseous stream rich in ethane; and (XII) recycling said fifth gaseous stream to said cracking step.

9. A process as defined in claim 1 wherein said cracked gas comprises a mixed olefin stream and said recovery step (b) comprises the steps of:

(i) compressing said mixed olefin stream to a pressure of from about 350 psig to about 520 psig to produce a compressed mixed olefin stream;

(ii) removing acid gas from said compressed mixed olefin stream with a caustic or amine acid gas removal system;

(iii) drying said acid gas removed mixed olefin stream over water-absorbing molecular sieve to a dew point of about −200° F. to produce a dried mixed olefin stream;

(iv) selectively hydrogenating the acetylenes in said dried mixed olefin stream to produce a hydrogenated mixed olefin stream;

(v) separating said hydrogenated mixted olefin-containing effluent in a demethanizer to produce a demethanizer overhead vapor effluent rich in methane and lighter gases and a demethanizer bottoms effluent rich in ethylene and heavier components;

(vi) separating the demethanizer bottoms in a deethanizer to produce a deethanizer overhead vapor effluent rich in ethane and ethylene and a deethanizer effluent bottoms rich in $C_{3+}$ hydrocarbons;

(vii) separating the deethanizer overhead vapor effluent in a $C_2$ splitter to produce a $C_2$ splitter overhead effluent comprising dilute ethylene and a $C_2$ splitter bottoms effluent rich in ethane;

(viii) separating the deethanizer bottoms effluent in a depropanizer to produce a depropanizer overhead vapor effluent rich in propane and propylene and a depropanizer bottoms effluent rich in $C_{4+}$ hydrocarbons;

(ix) separating said depropanizer overhead vapor effluent in a $C_3$ splitter to produce a $C_3$ splitter overhead effluent comprising dilute propylene and a $C_3$ splitter bottoms effluent rich in propane; and optionally;

(x) further separating said depropanizer bottoms effluent in at least one downstream fractionator into effluent streams comprising one or more of a $C_4$ hydrocarbon-rich stream and a gasoline-rich stream.

10. A process as defined in claim 1 wherein said cracked gas comprises a mixed olefin stream and said recovery step (b) comprises the steps of:

(i) compressing said mixed olefin stream to a pressure of from about 350 psig to about 520 psig to produce a compressed mixed olefin stream;

(ii) removing acid gas from said compressed mixed olefin stream with a caustic or amine acid gas removal system;

(iii) drying said acid gas removed mixed olefin stream over water-absorbing molecular sieve to a dew point of about −200° F. to produce a dried mixed olefin stream;

(iv) separating said dried mixed olefin stream in a demethanizer to produce a demethanizer overhead vapor effluent rich in methane and lighter gases and a demethanizer bottoms effluent rich in ethylene and heavier components;

(v) separating the demethanizer bottoms in a deethanizer to produce a deethanizer overhead vapor effluent rich in ethane and ethylene and a deethanizer effluent bottoms rich in $C_{3+}$ hydrocarbons;

(vi) selectively hydrogenating the acetylenes in said deethanizer overhead vapor to produce a hydrogenated deethanizer overhead vapor;

(vii) separating the hydrogenated deethanizer overhead vapor effluent in a $C_2$ splitter to produce a $C_2$ splitter overhead effluent comprising dilute ethylene and a $C_2$ splitter bottoms effluent rich in ethane;

(viii) separating the deethanizer bottoms effluent in a depropanizer to produce a depropanizer overhead vapor effluent rich in propane and propylene and a depropanizer bottoms effluent rich in $C_{4+}$ hydrocarbons;

(ix) separating said depropanizer overhead vapor effluent in a $C_3$ splitter to produce a $C_3$ splitter overhead effluent comprising dilute propylene and a $C_3$ splitter bottoms effluent rich in propane; and optionally;

(x) further separating said depropanizer bottoms effluent in at least one downstream fractionator into effluent streams comprising one or more of a $C_4$ hydrocarbon-rich stream and a gasoline-rich stream.

11. A process for the expansion of an existing process having a cracking capacity wherein said existing process produces polymer grade ethylene, polymer grade propylene or both, said expansion comprising modifying said existing process to a process as defined in claim 1 whereby the overall capacity of said existing process is increased.

12. A process as defined in claim 11 wherein said existing process comprises:

(i) cracking a hydrocarbon feedstock in a cracking reactor having a cracking capacity to produce a cracked product;

(ii) compressing said cracked product to produce a compressed gas stream;

(iii) removing acid gas from said compressed gas stream to produce an acid gas removed stream;

(iv) drying said acid gas removed stream to produce a dried gas stream;

(v) selectively hydrogenating the acetylenes in said dried gas stream to produce a hydrogenated gas stream;

(vi) separating said hydrogenated gas stream in a demethanizer to produce a demethanizer overhead vapor effluent rich in methane and lighter gases and a demethanizer bottoms effluent rich in ethylene and heavier components;

(vii) separating said demethanizer bottoms in a deethanizer to produce a deethanizer overhead vapor effluent rich in ethane and ethylene and a deethanizer bottoms rich in $C_{3+}$ hydrocarbons;

(viii) separating said deethanizer overhead effluent in a $C_2$ splitter to produce a $C_2$ splitter overhead effluent comprising polymer grade ethylene and a $C_2$ splitter bottoms effluent rich in ethane; and optionally (ix) separating the deethanizer bottoms effluent in a depropanizer to produce a depropanizer overhead effluent rich in propane and propylene and a depropanizer bottoms effluent rich in $C_{4+}$ hydrocarbons; and optionally (x) separating said depropanizer overhead vapor effluent in a $C_3$ splitter to produce a $C_3$ splitter overhead effluent comprising polymer grade propylene and a $C_3$ splitter bottoms rich in propane;

wherein said expansion comprises:

(I) increasing the capacity of said cracking step (i);

(II) modifying said step (vi) to comprise the following steps:

(a) dephlegmating or separating at least a portion of said hydrogenated gas to produce a primary methane-rich gas stream, a primary ethylene-rich liquid stream and a primary liquid condensate stream rich in $C_{2+}$ hydrocarbon components;

(b) separating said primary liquid condensate stream in a moderately low cryogenic temperature primary demethanizer into a $C_{2+}$ liquid bottoms stream and an intermediate methane-rich overhead vapor stream;

(c) separating the intermediate methane-rich overhead vapor stream and the primary ethylene rich liquid stream in an ultra low cryogenic temperature final demethanizer into a second dilute ethylene product stream and a final demethanizer methane vapor stream;

(d) separating said $C_{2+}$ liquid bottoms stream in at least one downstream fractionator into effluent streams comprising one or more of a dilute ethylene stream, a dilute propylene stream, an ethane-rich stream, a propane-rich stream, a $C_4$ hydrocarbon rich stream and a gasoline rich stream;

(III) processing either or both the dilute ethylene stream and dilute propylene stream to produce at least one ethylene derivative product and/or at least one propylene derivative product and by-products thereof; and (IV) recycling said by-products to said cracking step.

13. A process as defined in claim 1 wherein said processing step (c) comprises converting said dilute ethylene stream to polyethylene by a process comprising the steps of:

(1) polymerizing said ethylene to produce polyethylene and polymerization reaction by-products wherein said polymerization is carried out either (i) by a gas phase polymerization reaction wherein said dilute ethylene stream comprises at least about 95 weight percent ethylene, or (ii) by a solution phase polymerization wherein said dilute ethylene stream comprises at least about 85 weight percent ethylene; and (2) recovering said polyethylene product;

and wherein said recycling step (d) comprises recycling said polymerization by-products to said cracking step (a).

14. A process as defined in claim 13 wherein the polymerization by-products from said gas phase polymerization reaction are recycled to said recovery step (b) and at least a portion of said polymerization by-products are recycled from said recovery step (b) to said cracking step (a).

15. A process as defined in claim 1 wherein said processing step (c) comprises the steps of:

(i) utilizing said dilute ethylene stream in any high once through conversion process amenable to the use of dilute ethylene to produce the derived derivative product plus byproducts, (ii) recovering said derived derivative product;

(iii) recycling at least a portion of said byproducts to said cracking step (a).

16. A process as defined in claim 15 wherein said high once through conversion process is selected from the group consisting of polyethylene polymerization, ethylene dichloride production, alpha olefins production, ethyl benzene production, styrene production, acetaldehyde production, and combinations of one or more of the foregoing.

17. A process as defined in claim 1 wherein said processing step (c) comprises the steps of:

(i) polymerizing said dilute propylene stream to produce polypropylene and polypropylene polymerization by-products wherein said propylene polymerization is carried out either
  (1) by a bulk phase polymerization reaction wherein said propylene-containing stream comprises at least about 85 weight percent propylene, or
  (2) by a gas phase polymerization reaction wherein said propylene-containing stream comprises at least about 95 weight percent propylene;

(ii) recovering said polypropylene; and (iii) recycling at least a portion of propylene polymerization by-products to said cracking step (a).

18. A process as defined in claim 1 wherein said processing step (c) comprises the steps of:

(i) utilizing said dilute propylene stream in any high once-through conversion process amenable to the use of dilute propylene to produce the desired derivative product and by-products;

(ii) recovering said derivative product; and (iii) recycling said by-products to said cracking step (a).

19. A process as defined in claim 18 wherein said high once through conversion process is selected from the group consisting of polypropylene polymerization, acrylonitrile production, cumene production, propylene oxide production, isopropanol production, acrolein production, allyl chloride production, and combinations of one or more of the foregoing.

20. An integrated process for the production of polyethylene and polypropylene comprising the steps of:

(a) cracking a hydrocarbon feedstock in a cracking reactor to produce a cracked product comprising ethylene, ethane, methane, hydrogen, propylene, propane, other $C_3$ components, $C_4$ components and heavier compounds;

(b) separating ethylene from said cracked product to produce a dilute ethylene stream comprising at least about 85 weight percent ethylene and separating propylene from said cracked product to produce a dilute propylene stream comprising at least about 85 weight percent propylene;

(c) polymerizing ethylene in said ethylene-containing stream to produce polyethylene and polyethylene polymerization reaction by-products wherein said ethylene polymerization is carried out either
  (i) by a gas phase polymerization reaction wherein said dilute ethylene stream comprises at least about 95 weight percent ethylene, or
  (ii) by a solution phase polymerization reaction wherein said dilute ethylene stream comprises at least about 85 weight percent ethylene;

(d) recovering said polyethylene product;

(e) polymerizing propylene in said propylene-containing stream to produce polypropylene and polypropylene polymerization by-products wherein said propylene polymerization is carried out either
  (i) by a bulk phase polymerization reaction wherein said propylene-containing stream comprises at least about 85 weight percent propylene, or
  (ii) by a gas phase polymerization reaction wherein said propylene-containing stream comprises at least about 95 weight percent propylene;

(f) recovering said polypropylene; and (g) recycling said ethylene polymerization by-products to said cracking step (a) in the case of a gas phase ethylene polymerization reaction or recycling said polymerization by-products to said ethylene separation step (b) in the case of a solution phase ethylene polymerization reaction.

21. A process as defined in claim 20 wherein said ethylene polymerization reaction is a solution phase polymerization reaction, said ethylene and propylene separation step (b) comprises:

(I) compressing said cracked product stream to a pressure of from about 350 psig to about 520 psig to produce a compressed product stream;

(II) removing acid gas from said compressed product stream with a caustic or amine system to produce an acid gas removed product stream;

(III) drying said acid gas removed product stream over water-absorbing molecular sieve to a dew point of about −200° F. to produce a dried product stream;

(IV) removing $C_4$ and heavier components from said dried product stream in a depropanizer tower to produce a depropanized product stream and a $C_4$ and heavier stream;

(V) selectively hydrogenating the acetylenes in said dried product stream to produce a hydrogenated product stream;

(VI) dephlegmating said dried product stream to produce a first vapor stream substantially free of $C_{3+}$ hydrocarbons and a first liquid stream rich in $C_{2+}$ hydrocarbons;

(VII) further dephlegmating said first vapor stream to produce a second vapor stream comprising hydrogen and methane and a second liquid stream rich in methane and ethylene;

(VIII) separating said first liquid stream in a moderately low temperature demethanizer to produce a third vapor stream substantially free of $C_{3+}$ hydrocarbons and a third liquid stream rich in $C_{2+}$ hydrocarbons;

(IX) separating said second liquid stream and said third vapor stream in a low temperature demethanizer to produce a fourth vapor stream comprising substantially methane and a fourth liquid stream comprising dilute ethylene;

(X) separating said third liquid stream in a deethylenization tower to produce an overhead stream comprising dilute ethylene and a fifth liquid stream substantially free of ethylene;

(XI) recovering said fourth liquid stream and said overhead stream as said dilute ethylene stream;

(XII) separating said fifth liquid stream to produce a fifth vapor stream comprising recycle ethane and a sixth liquid stream rich in $C_3$ hydrocarbons;

(XIII) separating said sixth liquid stream to produce a dilute propylene overhead stream and a bottoms propane stream; and (XIV) recycling said bottoms propane stream to said steam cracking step.

22. A process as defined in claim 20 wherein said by-products from polypropylene polymerization step are recycled to said separation step (XII).

23. A process as defined in claim 1 wherein said $C_4$ and heavier stream comprising one or more of ethyl acetylene, vinyl acetylene, 1,3-butadiene, 1,2-butadiene, isobutylene, cis-2-butene, trans-2-butene, 1-butene, isobutane, and n-butane is recovered from said cracked product stream and processed in a $C_4$ processing system comprising:

(A) catalytically hydrogenating ethyl acetylene, vinyl acetylene, 1,3-butadiene and 1,2-butadiene to butenes and catalytically converting 1-butene to 2-butenes in the presence of a catalyst comprising at least one hydrogenating metal and a moderately acidic carrier at a temperature ranging from about 40° C. to about 400° C. and a pressure ranging from about 1 to about 100 bars in a hydroisomerization zone to produce a hydrogenated stream comprising isobutylene, 1-butene, 2-butenes and $C_4$ paraffins;

(B) reacting isobutylene in the hydrogenated stream either
 (1) with methanol in a methyl tertiary butyl ether synthesis zone in the presence of an acid type ion exchange resin catalyst at a temperature ranging from about 60° F. to about 300° F. and a pressure ranging from about 80 to 400 psig to produce a methyl tertiary butyl ether-rich product effluent and a by-product effluent comprising $C_4$ paraffins and $C_4$ olefins, or
 (2) polymerizing said isobutylene in a polymerization zone to produce a polyisobutylene-rich product effluent and a by-product effluent comprising $C_4$ paraffins and $C_4$ olefins;

(C) separating the $C_4$ paraffins from the $C_4$ olefins in said by-product effluent in a paraffin/olefin separation zone to produce a $C_4$ paraffin-rich effluent and a $C_4$ olefin-rich effluent comprising 1-butene and 2-butenes;

(D) catalytically converting 2-butenes in said $C_4$ olefin rich effluent to isobutylene in a skeletal isomerization zone in the presence of an acidic catalyst at a pressure of about atmospheric and a temperature ranging from about 600° F. to about 1100° F. to produce a skeletal isomerized effluent;

(E) recycling said skeletal isomerized effluent to step (A) or step (B); and (F) where methyl tertiary butyl ether is produced in step (B) either
 (1) recovering said methyl tertiary butyl ether as product; or
 (2) producing methyl methacrylate from the methyl tertiary butyl ether by a process comprising:
  (i) decomposing said methyl tertiary butyl ether into a methanol-containing stream and an isobutylene-containing stream,
  (ii) catalytically oxidizing the isobutylene over a complex molybdenum oxide catalyst at temperatures ranging from about 350 to about 450° C. and from about 15 to about 25 psig to produce methacrolein,
  (iii) oxidizing the methacrolein over a molybdenum catalyst at temperatures of from about 250 to about 350° C. and from about 15 to about 25 psig to produce methacrylic acid,
  (iv) esterifying the methacrylic acid with methanol to produce methyl methacrylate, or (3) producing butyl rubber from the methyl tertiary butyl ether by a process comprising:
  (i) decomposing said methyl tertiary butyl ether into a methanol-containing stream and an isobutylene-containing stream,
  (ii) cationically copolymerizing the isobutylene in said isobutylene-containing stream with isoprene at temperatures ranging from about −30 to about −100° F. in the presence of a Lewis acid catalyst and a small amount of water as a cocatalyst, and
  (iii) recovering butyl rubber product; or (G) where polyisobutylene is produced in step (B)(2), recovering said polyisobutylene product.

24. An integrated process for the processing a mixed $C_4$ hydrocarbon feedstock comprising ethyl acetylene, vinyl acetylene, 1,3-butadiene, 1,2-butadiene, isobutylene, cis-2-butene, trans-2-butene, 1-butene, isobutane and n-butane, said process comprising the following process steps conducted in sequence:

(A) catalytically hydrogenating ethyl acetylene, vinyl acetylene, 1,3-butadiene and 1,2-butadiene to butenes and catalytically converting 1-butene to 2-butenes in the presence of a catalyst comprising at least one hydrogenating metal and a moderately acidic carrier at a temperature ranging from about 40° C. to about 400° C. and a pressure ranging from about 1 to about 100 bars in a hydroisomerization zone to produce a hydrogenated stream comprising isobutylene, 1-butene, 2-butenes and $C_4$ paraffins;

(B) reacting isobutylene in the hydrogenated stream either
 (1) with methanol in a methyl tertiary butyl ether synthesis zone in the presence of an acid type ion exchange resin catalyst at a temperature ranging from about 60° F. to about 300° F. and a pressure ranging from about 80 to 400 psig to produce a methyl tertiary butyl ether-rich product effluent and a by-product effluent comprising $C_4$ paraffins and $C_4$ olefins, or
 (2) polymerizing said isobutylene in a polymerization zone to produce a polyisobutylene-rich product effluent and a by-product effluent comprising $C_4$ paraffins and $C_4$ olefins;

(C) separating the $C_4$ paraffins from the $C_4$ olefins in said by-product effluent in a paraffin/olefin separation zone to produce a $C_4$ paraffin-rich effluent and a $C_4$ olefin-rich effluent comprising 1-butene and 2-butenes;

(D) catalytically converting 2-butenes in said $C_4$ olefin rich effluent to isobutylene in a skeletal isomerization zone in the presence of an acidic catalyst at a pressure of about atmospheric and a temperature ranging from about 600° F. to about 1100° F. to produce a skeletal isomerized effluent;

(E) recycling said skeletal isomerized effluent to step (A) or step (B); and (F) where methyl tertiary butyl ether is produced in step (B) either
 (1) producing methyl methacrylate from the methyl tertiary butyl ether by a process comprising:
  (i) decomposing said methyl tertiary butyl ether into a methanol-containing stream and an isobutylene-containing stream,
  (ii) catalytically oxidizing the isobutylene over a complex molybdenum oxide catalyst at temperatures ranging from about 350 to about 450° C. and from about 15 to about 25 psig to produce methacrolein, (iii) oxidizing the methacrolein over a molybdenum catalyst at temperatures of from about 250 to about 350° C. and from about 15 to about 25 psig to produce methacrylic acid,
(iv) esterifying the methacrylic acid with methanol to produce methyl methacrylate, or (2) producing butyl rubber from the methyl tertiary butyl ether by a process comprising:
(i) decomposing said methyl tertiary butyl ether into a methanol-containing stream and an isobutylene-containing stream,
(ii) cationically copolymerizing the isobutylene in said isobutylene-containing stream with isoprene at temperatures ranging from about −30 to about −100° F. in the presence of a Lewis acid catalyst and a small amount of water as a cocatalyst, and
(iii) recovering butyl rubber product; or (G) where polyisobutylene is produced in step (B)(2), recovering said polyisobutylene product.

* * * * *